US012625145B2

(12) United States Patent
Salumets et al.

(10) Patent No.: US 12,625,145 B2
(45) Date of Patent: May 12, 2026

(54) ENDOMETRIAL RECEPTIVITY DETERMINATION

(71) Applicant: Celvia CC AS, Tartu (EE)

(72) Inventors: Andres Salumets, Tartu (EE); Sergo Kasvandik, Tartu (EE); Maire Peters, Tartu (EE); Tanel Kaart, Tartu (EE)

(73) Assignee: Celvia CC AS, Tartu (EE)

( * ) Notice: Subject to any disclaimer, the term of this patent is extended or adjusted under 35 U.S.C. 154(b) by 1212 days.

(21) Appl. No.: 17/611,706

(22) PCT Filed: May 11, 2020

(86) PCT No.: PCT/EP2020/063066
§ 371 (c)(1),
(2) Date: Nov. 16, 2021

(87) PCT Pub. No.: WO2020/234026
PCT Pub. Date: Nov. 26, 2020

(65) Prior Publication Data
US 2022/0196670 A1     Jun. 23, 2022

(30) Foreign Application Priority Data
May 17, 2019     (SE) .................................... 1950592-4

(51) Int. Cl.
*G01N 33/68*            (2006.01)

(52) U.S. Cl.
CPC ....... *G01N 33/689* (2013.01); *G01N 2570/00* (2013.01); *G01N 2800/367* (2013.01)

(58) Field of Classification Search
None
See application file for complete search history.

(56) References Cited

U.S. PATENT DOCUMENTS 10,081,840 B2     9/2018   Simón ValléS et al.
2012/0040849 A1 *  2/2012   Simon .................. C12Q 1/6883
                                                          506/7

FOREIGN PATENT DOCUMENTS

WO     2018/096375 A2     5/2018
WO     2018/198054 A1     11/2018

OTHER PUBLICATIONS

Salomensen et al., Fertil Steril, 2013;99:1086-92 (Year: 2013).*
Piomboni et al., Human Reproduction (Oxford), (Jul. 2018) vol. 33, No. Suppl. 1, p. 358, Abstract P-472 (Year: 2018).*
Wetendorf et al., Biology of reproduction, (Feb. 1, 2017) vol. 96, No. 2, pp. 313-326 (Year: 2017).*
Boggavarapu et al., Scientific Reports, 2016; 6: 33811 (Year: 2016).*
Burns, Gregory et. al., Extracellular Vesicles in Luminal Fluid of the Ovine Uterus, PLOS One, vol. 9, No. 3, pp. 1-11 (Mar. 10, 2014).
Chan, Crystal et al., Discovery of biomarkers of endometrial receptivity through a minimally invasive approach: a validation study with implications for assisted reproduction, Fertility and Sterility, vol. 100, No. 3, pp. 810-817 (May 30, 2013).
Hannan, Natalie J. et al., 2D-DiGE Analysis of the Human Endometrial Secretome Reveals Differences between Receptive and Nonreceptive States in Fertile and Infertile Women, Journal of Proteome Research, vol. 9, No. 12, pp. 6256-6264 (Dec. 3, 2010).
Kasvandik, Sergo et al., Uterine Fluid Proteins for Minimally Invasive Assessment of Endometrial Receptivity, Journal of Clinical Endocrinology and Metabolism, vol. 105, No. 1, pp. 219-230 (Jan. 1, 2020).
Liu, Yue-Fang et al., Progesterone induces the expression of lipocalin-2 through Akt-c-Myc pathway during mouse decidualization, FEBS Letters, vol. 590, No. 16, pp. 2594-2602 (Jul. 29, 2016).
Qiao, Jie et al., Microarray evaluation of endometrial receptivity in Chinese women with polycystic ovary syndrome, Reproductive BioMedicine Online, vol. 17, No. 3, pp. 425-435 (Sep. 1, 2008).

* cited by examiner

*Primary Examiner* — Christina M Borgeest
(74) *Attorney, Agent, or Firm* — Porter Wright Morris & Arthur LLP

(57)                    ABSTRACT
Endometrial receptivity status is determined by measuring, in an uterine fluid sample taken from a woman, the amounts of at least three proteins selected among NNMT, LCN2, PGR, SLC26A2, SLC34A2, TCN1, ENPP3, GRN, STC1, DPP4, MPO, CD55, ELANE, MSLN, CTSB, RNASET2, CRISP3, MVP, MMP26, AOC1 and SDCBP2. The EM receptivity status of the woman is determined based on a comparison of the measured amounts of the at least three proteins with respective control amounts.

11 Claims, 20 Drawing Sheets

Specification includes a Sequence Listing.

|  | ESE / MSE | MSE / RIF MSE |
|---|---|---|
| Sensitivity | 91.7% | 96.7% |
| Specificity | 91.7% | 91.7% |

SEQUENCE LISTING

```
<160> NUMBER OF SEQ ID NOS: 81

<210> SEQ ID NO 1
<211> LENGTH: 12
<212> TYPE: PRT
<213> ORGANISM: Homo sapiens

<400> SEQUENCE: 1

Glu Glu Ile Phe Gly Pro Val Gln Pro Ile Leu Lys
1               5                   10

<210> SEQ ID NO 2
<211> LENGTH: 11
<212> TYPE: PRT
<213> ORGANISM: Homo sapiens

<400> SEQUENCE: 2

Ile Ala Phe Thr Gly Ser Thr Glu Val Gly Lys
1               5                   10

<210> SEQ ID NO 3
```

```
<211> LENGTH: 10
<212> TYPE: PRT
<213> ORGANISM: Homo sapiens

<400> SEQUENCE: 3

Phe Tyr Gly Ser Pro Glu Glu Leu Ala Arg
1               5                   10

<210> SEQ ID NO 4
<211> LENGTH: 11
<212> TYPE: PRT
<213> ORGANISM: Homo sapiens

<400> SEQUENCE: 4

Asp Leu Ile Val Thr Pro Ala Thr Ile Leu Lys
1               5                   10

<210> SEQ ID NO 5
<211> LENGTH: 7
<212> TYPE: PRT
<213> ORGANISM: Homo sapiens

<400> SEQUENCE: 5

Glu Val Val Gly Thr Phe Lys
1               5

<210> SEQ ID NO 6
<211> LENGTH: 10
<212> TYPE: PRT
<213> ORGANISM: Homo sapiens

<400> SEQUENCE: 6

Asn Gly Glu Val Gln Asn Leu Ala Val Lys
1               5                   10

<210> SEQ ID NO 7
<211> LENGTH: 6
<212> TYPE: PRT
<213> ORGANISM: Homo sapiens

<400> SEQUENCE: 7

Gly Ile Pro Val Tyr Arg
1               5

<210> SEQ ID NO 8
<211> LENGTH: 9
<212> TYPE: PRT
<213> ORGANISM: Homo sapiens

<400> SEQUENCE: 8

Asp Leu Thr Cys Leu Gln Asn Leu Lys
1               5

<210> SEQ ID NO 9
<211> LENGTH: 9
<212> TYPE: PRT
<213> ORGANISM: Homo sapiens

<400> SEQUENCE: 9

Ser Cys Pro Asn Pro Gly Glu Ile Arg
1               5

<210> SEQ ID NO 10
<211> LENGTH: 22
<212> TYPE: PRT
```

```
<213> ORGANISM: Homo sapiens

<400> SEQUENCE: 10

Leu Val Tyr Ser Ile Leu Glu Gly Gln Pro Tyr Phe Ser Val Glu Ala
1               5                   10                  15

Gln Thr Gly Ile Ile Arg
            20

<210> SEQ ID NO 11
<211> LENGTH: 10
<212> TYPE: PRT
<213> ORGANISM: Homo sapiens

<400> SEQUENCE: 11

Val Leu Asp Val Asn Asp Asn Ala Pro Lys
1               5                   10

<210> SEQ ID NO 12
<211> LENGTH: 13
<212> TYPE: PRT
<213> ORGANISM: Homo sapiens

<400> SEQUENCE: 12

Asp Leu Val Leu Ser Glu Pro Ser Ser Gln Ser Leu Arg
1               5                   10

<210> SEQ ID NO 13
<211> LENGTH: 10
<212> TYPE: PRT
<213> ORGANISM: Homo sapiens

<400> SEQUENCE: 13

Ser Ser Thr Gly Pro Gly Glu Gln Leu Arg
1               5                   10

<210> SEQ ID NO 14
<211> LENGTH: 8
<212> TYPE: PRT
<213> ORGANISM: Homo sapiens

<400> SEQUENCE: 14

Trp Ala Asn Gln Cys Asn Tyr Arg
1               5

<210> SEQ ID NO 15
<211> LENGTH: 8
<212> TYPE: PRT
<213> ORGANISM: Homo sapiens

<400> SEQUENCE: 15

Leu Pro Ala Ser Phe Asp Ala Arg
1               5

<210> SEQ ID NO 16
<211> LENGTH: 18
<212> TYPE: PRT
<213> ORGANISM: Homo sapiens

<400> SEQUENCE: 16

Asn Gly Pro Val Glu Gly Ala Phe Ser Val Tyr Ser Asp Phe Leu Leu
1               5                   10                  15

Tyr Lys
```

-continued

```
<210> SEQ ID NO 17
<211> LENGTH: 12
<212> TYPE: PRT
<213> ORGANISM: Homo sapiens

<400> SEQUENCE: 17

Leu Ala Tyr Val Trp Asn Asn Asp Ile Tyr Val Lys
1               5                   10

<210> SEQ ID NO 18
<211> LENGTH: 14
<212> TYPE: PRT
<213> ORGANISM: Homo sapiens

<400> SEQUENCE: 18

Leu Gly Thr Phe Glu Val Glu Asp Gln Ile Glu Ala Ala Arg
1               5                   10

<210> SEQ ID NO 19
<211> LENGTH: 11
<212> TYPE: PRT
<213> ORGANISM: Homo sapiens

<400> SEQUENCE: 19

Ile Gly Gly Ile Gly Thr Val Pro Val Gly Arg
1               5                   10

<210> SEQ ID NO 20
<211> LENGTH: 8
<212> TYPE: PRT
<213> ORGANISM: Homo sapiens

<400> SEQUENCE: 20

Gln Leu Ile Val Gly Val Asn Lys
1               5

<210> SEQ ID NO 21
<211> LENGTH: 10
<212> TYPE: PRT
<213> ORGANISM: Homo sapiens

<400> SEQUENCE: 21

Val Val Leu Gly Ala His Asn Leu Ser Arg
1               5                   10

<210> SEQ ID NO 22
<211> LENGTH: 13
<212> TYPE: PRT
<213> ORGANISM: Homo sapiens

<400> SEQUENCE: 22

Val His Leu Phe Val Asp Gln Gln Trp Leu Ala Val Arg
1               5                   10

<210> SEQ ID NO 23
<211> LENGTH: 8
<212> TYPE: PRT
<213> ORGANISM: Homo sapiens

<400> SEQUENCE: 23

Glu Tyr Val Ser Gly Phe Gly Lys
1               5

<210> SEQ ID NO 24
<211> LENGTH: 12
```

```
<212> TYPE: PRT
<213> ORGANISM: Homo sapiens

<400> SEQUENCE: 24

Ala Ile Ala His Tyr Glu Gln Gln Met Gly Gln Lys
1               5                   10

<210> SEQ ID NO 25
<211> LENGTH: 13
<212> TYPE: PRT
<213> ORGANISM: Homo sapiens

<400> SEQUENCE: 25

Glu Val Val Ser Ala Gln Pro Ala Thr Phe Leu Ala Arg
1               5                   10

<210> SEQ ID NO 26
<211> LENGTH: 10
<212> TYPE: PRT
<213> ORGANISM: Homo sapiens

<400> SEQUENCE: 26

Gly Ser Glu Ile Val Ala Gly Leu Glu Lys
1               5                   10

<210> SEQ ID NO 27
<211> LENGTH: 15
<212> TYPE: PRT
<213> ORGANISM: Homo sapiens

<400> SEQUENCE: 27

Val Gly Ala His Ala Gly Glu Tyr Gly Ala Glu Ala Leu Glu Arg
1               5                   10                  15

<210> SEQ ID NO 28
<211> LENGTH: 12
<212> TYPE: PRT
<213> ORGANISM: Homo sapiens

<400> SEQUENCE: 28

Phe Leu Ala Ser Val Ser Thr Val Leu Thr Ser Lys
1               5                   10

<210> SEQ ID NO 29
<211> LENGTH: 10
<212> TYPE: PRT
<213> ORGANISM: Homo sapiens

<400> SEQUENCE: 29

Phe Ser Ile Asp Val Phe Glu Glu Thr Arg
1               5                   10

<210> SEQ ID NO 30
<211> LENGTH: 11
<212> TYPE: PRT
<213> ORGANISM: Homo sapiens

<400> SEQUENCE: 30

Gln Val Pro Gly Gly Tyr Thr Val Ile Asn Lys
1               5                   10

<210> SEQ ID NO 31
<211> LENGTH: 17
<212> TYPE: PRT
<213> ORGANISM: Homo sapiens
```

-continued

```
<400> SEQUENCE: 31

Ala Gly Ala Ala Ala Gly Gly Pro Gly Val Ser Gly Val Cys Val Cys
1               5                   10                  15

Lys

<210> SEQ ID NO 32
<211> LENGTH: 14
<212> TYPE: PRT
<213> ORGANISM: Homo sapiens

<400> SEQUENCE: 32

His Glu Val Thr Gly Trp Val Leu Val Ser Pro Leu Ser Lys
1               5                   10

<210> SEQ ID NO 33
<211> LENGTH: 10
<212> TYPE: PRT
<213> ORGANISM: Homo sapiens

<400> SEQUENCE: 33

Ile Leu Asp Tyr Glu Val Thr Leu Thr Arg
1               5                   10

<210> SEQ ID NO 34
<211> LENGTH: 9
<212> TYPE: PRT
<213> ORGANISM: Homo sapiens

<400> SEQUENCE: 34

Leu Thr Trp Thr Asn Pro Ser Ile Lys
1               5

<210> SEQ ID NO 35
<211> LENGTH: 9
<212> TYPE: PRT
<213> ORGANISM: Homo sapiens

<400> SEQUENCE: 35

Val Phe Val Gly Gly Asp Asp Phe Lys
1               5

<210> SEQ ID NO 36
<211> LENGTH: 8
<212> TYPE: PRT
<213> ORGANISM: Homo sapiens

<400> SEQUENCE: 36

Phe Ser Tyr Leu Pro Ile Gln Lys
1               5

<210> SEQ ID NO 37
<211> LENGTH: 7
<212> TYPE: PRT
<213> ORGANISM: Homo sapiens

<400> SEQUENCE: 37

Glu Leu Thr Ser Glu Leu Lys
1               5

<210> SEQ ID NO 38
<211> LENGTH: 11
<212> TYPE: PRT
<213> ORGANISM: Homo sapiens
```

<400> SEQUENCE: 38

```
Ser Tyr Pro Gly Leu Thr Ser Tyr Leu Val Arg
1               5                   10
```

<210> SEQ ID NO 39
<211> LENGTH: 13
<212> TYPE: PRT
<213> ORGANISM: Homo sapiens

<400> SEQUENCE: 39

```
Leu Ser Ala Leu Ser Ala Gly Ser Asn Glu Tyr Leu Arg
1               5                   10
```

<210> SEQ ID NO 40
<211> LENGTH: 8
<212> TYPE: PRT
<213> ORGANISM: Homo sapiens

<400> SEQUENCE: 40

```
Ile Gln His Leu Tyr Gly Glu Lys
1               5
```

<210> SEQ ID NO 41
<211> LENGTH: 11
<212> TYPE: PRT
<213> ORGANISM: Homo sapiens

<400> SEQUENCE: 41

```
Thr Phe Gln Leu Ser Ala Asp Asp Ile Gln Arg
1               5                   10
```

<210> SEQ ID NO 42
<211> LENGTH: 10
<212> TYPE: PRT
<213> ORGANISM: Homo sapiens

<400> SEQUENCE: 42

```
Ile Ala Asn Val Phe Thr Asn Ala Phe Arg
1               5                   10
```

<210> SEQ ID NO 43
<211> LENGTH: 9
<212> TYPE: PRT
<213> ORGANISM: Homo sapiens

<400> SEQUENCE: 43

```
Ser Pro Thr Leu Gly Ala Ser Asn Arg
1               5
```

<210> SEQ ID NO 44
<211> LENGTH: 14
<212> TYPE: PRT
<213> ORGANISM: Homo sapiens

<400> SEQUENCE: 44

```
Ile Gln Ser Phe Leu Gly Gly Ala Pro Thr Glu Asp Leu Lys
1               5                   10
```

<210> SEQ ID NO 45
<211> LENGTH: 10
<212> TYPE: PRT
<213> ORGANISM: Homo sapiens

<400> SEQUENCE: 45

```
Leu Leu Gly Pro His Val Glu Gly Leu Lys
1               5               10

<210> SEQ ID NO 46
<211> LENGTH: 13
<212> TYPE: PRT
<213> ORGANISM: Homo sapiens

<400> SEQUENCE: 46

Ala Leu Gln Pro Leu Glu Glu Gly Glu Asp Glu Glu Lys
1               5               10

<210> SEQ ID NO 47
<211> LENGTH: 11
<212> TYPE: PRT
<213> ORGANISM: Homo sapiens

<400> SEQUENCE: 47

Ile Glu Gly Glu Gly Ser Val Leu Gln Ala Lys
1               5               10

<210> SEQ ID NO 48
<211> LENGTH: 10
<212> TYPE: PRT
<213> ORGANISM: Homo sapiens

<400> SEQUENCE: 48

Asp Thr Tyr Leu Ser His Phe Asn Pro Arg
1               5               10

<210> SEQ ID NO 49
<211> LENGTH: 8
<212> TYPE: PRT
<213> ORGANISM: Homo sapiens

<400> SEQUENCE: 49

Phe Ser Ser Leu Pro Leu Gly Arg
1               5

<210> SEQ ID NO 50
<211> LENGTH: 9
<212> TYPE: PRT
<213> ORGANISM: Homo sapiens

<400> SEQUENCE: 50

His Ser Ala Glu Ser Gln Ile Leu Lys
1               5

<210> SEQ ID NO 51
<211> LENGTH: 9
<212> TYPE: PRT
<213> ORGANISM: Homo sapiens

<400> SEQUENCE: 51

His Leu Trp Tyr Leu Leu Asp Leu Lys
1               5

<210> SEQ ID NO 52
<211> LENGTH: 7
<212> TYPE: PRT
<213> ORGANISM: Homo sapiens

<400> SEQUENCE: 52

Gln Asp Leu Glu Leu Pro Lys
```

-continued

```
1               5

<210> SEQ ID NO 53
<211> LENGTH: 11
<212> TYPE: PRT
<213> ORGANISM: Homo sapiens

<400> SEQUENCE: 53

Gly Ala Pro Pro Leu Gln Val Gln Trp Phe Arg
1               5                   10

<210> SEQ ID NO 54
<211> LENGTH: 12
<212> TYPE: PRT
<213> ORGANISM: Homo sapiens

<400> SEQUENCE: 54

Tyr Ala Ala Leu Ser Asp Gln Gly Leu Asp Ile Lys
1               5                   10

<210> SEQ ID NO 55
<211> LENGTH: 8
<212> TYPE: PRT
<213> ORGANISM: Homo sapiens

<400> SEQUENCE: 55

Pro Gly Phe Val Ile Gln Leu Arg
1               5

<210> SEQ ID NO 56
<211> LENGTH: 12
<212> TYPE: PRT
<213> ORGANISM: Homo sapiens

<400> SEQUENCE: 56

Leu Glu Leu Gly Asn Asp Trp Asp Ser Ala Thr Lys
1               5                   10

<210> SEQ ID NO 57
<211> LENGTH: 16
<212> TYPE: PRT
<213> ORGANISM: Homo sapiens

<400> SEQUENCE: 57

Gln Leu Leu Gly Leu Gln Pro Ile Ser Thr Val Ser Pro Leu His Arg
1               5                   10                  15

<210> SEQ ID NO 58
<211> LENGTH: 11
<212> TYPE: PRT
<213> ORGANISM: Homo sapiens

<400> SEQUENCE: 58

Ala Pro Gly Ala Ser Gly Cys Leu Leu Pro Arg
1               5                   10

<210> SEQ ID NO 59
<211> LENGTH: 14
<212> TYPE: PRT
<213> ORGANISM: Homo sapiens

<400> SEQUENCE: 59

Val Ala Leu Val Glu Gln Asp Ala Pro Met Ala Pro Gly Arg
1               5                   10
```

```
<210> SEQ ID NO 60
<211> LENGTH: 14
<212> TYPE: PRT
<213> ORGANISM: Homo sapiens

<400> SEQUENCE: 60

Val Leu Leu Leu Leu Asn Thr Ile Pro Leu Glu Gly Leu Arg
1               5               10

<210> SEQ ID NO 61
<211> LENGTH: 14
<212> TYPE: PRT
<213> ORGANISM: Homo sapiens

<400> SEQUENCE: 61

Phe Tyr Gly Pro Glu Gly Pro Tyr Gly Val Phe Ala Gly Arg
1               5               10

<210> SEQ ID NO 62
<211> LENGTH: 9
<212> TYPE: PRT
<213> ORGANISM: Homo sapiens

<400> SEQUENCE: 62

Gly Leu Ala Thr Phe Cys Leu Asp Lys
1               5

<210> SEQ ID NO 63
<211> LENGTH: 8
<212> TYPE: PRT
<213> ORGANISM: Homo sapiens

<400> SEQUENCE: 63

Ile Leu Leu Asn Pro Gln Asp Lys
1               5

<210> SEQ ID NO 64
<211> LENGTH: 8
<212> TYPE: PRT
<213> ORGANISM: Homo sapiens

<400> SEQUENCE: 64

Val Tyr Thr Val Asp Leu Gly Arg
1               5

<210> SEQ ID NO 65
<211> LENGTH: 12
<212> TYPE: PRT
<213> ORGANISM: Homo sapiens

<400> SEQUENCE: 65

Ile Ile Asp Gly Val Pro Val Glu Ile Thr Glu Lys
1               5               10

<210> SEQ ID NO 66
<211> LENGTH: 13
<212> TYPE: PRT
<213> ORGANISM: Homo sapiens

<400> SEQUENCE: 66

Ile Ser Thr Gly Gly Gly Glu Thr Glu Glu Thr Leu Lys
1               5               10

<210> SEQ ID NO 67
```

-continued

```
<211> LENGTH: 10
<212> TYPE: PRT
<213> ORGANISM: Homo sapiens

<400> SEQUENCE: 67

Glu Leu Asp Leu Asn Ser Val Leu Leu Lys
1               5                   10

<210> SEQ ID NO 68
<211> LENGTH: 10
<212> TYPE: PRT
<213> ORGANISM: Homo sapiens

<400> SEQUENCE: 68

Ser Trp Pro Phe Asn Leu Glu Glu Ile Lys
1               5                   10

<210> SEQ ID NO 69
<211> LENGTH: 8
<212> TYPE: PRT
<213> ORGANISM: Homo sapiens

<400> SEQUENCE: 69

Val His Leu Ser Asp Ser Glu Arg
1               5

<210> SEQ ID NO 70
<211> LENGTH: 11
<212> TYPE: PRT
<213> ORGANISM: Homo sapiens

<400> SEQUENCE: 70

Phe Gly Asp Gln Leu Leu Gln Ile Asp Gly Arg
1               5                   10

<210> SEQ ID NO 71
<211> LENGTH: 10
<212> TYPE: PRT
<213> ORGANISM: Homo sapiens

<400> SEQUENCE: 71

Val Asp Gln Ala Ile Gln Ala Gln Val Arg
1               5                   10

<210> SEQ ID NO 72
<211> LENGTH: 10
<212> TYPE: PRT
<213> ORGANISM: Homo sapiens

<400> SEQUENCE: 72

Ser Gln Tyr Leu Leu Thr Ala Ile His Lys
1               5                   10

<210> SEQ ID NO 73
<211> LENGTH: 8
<212> TYPE: PRT
<213> ORGANISM: Homo sapiens

<400> SEQUENCE: 73

Leu Cys His Asn Val Gly Tyr Lys
1               5

<210> SEQ ID NO 74
<211> LENGTH: 18
<212> TYPE: PRT
```

```
<213> ORGANISM: Homo sapiens

<400> SEQUENCE: 74

Gly Val Cys Ile Ser Pro Glu Ala Ile Val Thr Asp Leu Pro Glu Asp
1               5                   10                  15

Val Lys

<210> SEQ ID NO 75
<211> LENGTH: 13
<212> TYPE: PRT
<213> ORGANISM: Homo sapiens

<400> SEQUENCE: 75

Ser Gly Cys Asn Glu Val Thr Thr Val Val Asp Val Lys
1               5                   10

<210> SEQ ID NO 76
<211> LENGTH: 10
<212> TYPE: PRT
<213> ORGANISM: Homo sapiens

<400> SEQUENCE: 76

Phe Val Ala Pro Leu Tyr Tyr Ile Asn Lys
1               5                   10

<210> SEQ ID NO 77
<211> LENGTH: 9
<212> TYPE: PRT
<213> ORGANISM: Homo sapiens

<400> SEQUENCE: 77

Gln Thr Val Asn Pro Ile Leu Ile Lys
1               5

<210> SEQ ID NO 78
<211> LENGTH: 15
<212> TYPE: PRT
<213> ORGANISM: Homo sapiens

<400> SEQUENCE: 78

Tyr Leu Glu Gly Ala Ala Gly Gln Gln Pro Thr Ala Pro Asp Lys
1               5                   10                  15

<210> SEQ ID NO 79
<211> LENGTH: 11
<212> TYPE: PRT
<213> ORGANISM: Homo sapiens

<400> SEQUENCE: 79

Val Ala Ala Gln Asn Ser Ala Glu Val Val Arg
1               5                   10

<210> SEQ ID NO 80
<211> LENGTH: 12
<212> TYPE: PRT
<213> ORGANISM: Homo sapiens

<400> SEQUENCE: 80

Gly Thr Ser Ala Val Asn Val Val Leu Ser Leu Lys
1               5                   10

<210> SEQ ID NO 81
<211> LENGTH: 8
<212> TYPE: PRT
```

-continued

```
<213> ORGANISM: Homo sapiens

<400> SEQUENCE: 81

Asn Gly Glu Asn Leu Glu Val Arg
1               5
```

1

ENDOMETRIAL RECEPTIVITY DETERMINATION

The sequence listing submitted herewith, entitled "Nov-15-2021-Sequence-Listing_ST25.txt", created Nov. 15, 2021 and having a size of 13,687 bytes, is incorporated herein by reference.

TECHNICAL FIELD

The present invention generally relates to determination of endometrial receptivity, and in particular to a uterine fluid protein panel that can be used in such a determination.

BACKGROUND

The uterine micromilieu and its main medium, the uterine fluid (UF), play an important role in reproductive success, influencing sperm movement through the uterus to the fallopian tubes, embryo development and implantation processes. The UF is a complex mixture of molecules secreted primarily by the endometrial (EM) glandular epithelial cells, but also by the immune cells and exosomes derived from EM cells. Additionally, detached or non-adherent cells and passively diffused molecules may likely contribute to the final repertoire of molecules found in the UF. The lower molecular weight fraction has been described to consist of compounds, such as amino acids, lactate, pyruvate, oxygen, glucose, antioxidants, ions, growth factors, hormones and lipids. To date, high-throughput proteomics studies have established that the UF contains at least 600-1,500 different proteins, depending on the sampling procedures and analysis methods used. The proteomic component of the UF reflects not only protein expression patterns in the EM tissue but may also contain components from other reproductive tract fluids, such as cervicovaginal fluid and fallopian tubes or even of peritoneal origin.

Regardless of the origin of the compounds identified in the UF, all of them provide a suitable buffer for the developing embryo in transit and facilitate its arrival to the correct intrauterine location for subsequent implantation. During the menstrual cycle, successful implantation is considered to be possible in a short period of time, known as the window of implantation (WOI), starting on cycle days 19 or 20 and lasting for about 4-5 days. Determination of the WOI has an utmost importance in the in vitro fertilization (IVF) procedure to increase chances of successful commencement of pregnancy.

Recurrent implantation failure (RIF) patients form one of the most complex groups of patients whose conception are cumbersome and can require large amount of resources and time, while causing emotional stress to both infertile couples and clinicians. RIF is defined when at least three implantation failures with good quality embryo transfers have occurred or when conception was not achieved after transfer of at least ten good-quality embryos. In some patients with RIF, WOI may be temporally displaced, leading to asynchrony between the developing embryo and the EM tissue that may result in implantation failure. Alternatively, the endometrial RIF may also arise from a molecularly disrupted WOI without a temporal shift.

Currently, there are few approaches in clinical use that enable determination of EM receptivity by gene expression profiling of endometrial tissue. U.S. Pat. No. 10,081,840 discloses an endometrial receptivity array (ERA) that allows evaluation of the receptive state of a human endometrium. ERA requires taking an endometrial sample by biopsy from the fundus of the uterus of a woman 7 days after her endogenous luteinizing hormone (LH) surge (LH+7) and then measuring the expression of 238 genes from the tissue sample. The endometrium is determined to be receptive based on a fold change greater than or equal to about three for the 238 genes when compared to a non-receptive endometrial sample.

The gene expression profiling methods exemplified by ERA, however, are invasive methods requiring taking an EM tissue sample. This means that such biopsy-based methods exclude embryo transfer during the same menstrual cycle as biopsy sampling.

WO 2018/198054 discloses a method and a diagnostic kit for analyzing the inflammatory state and endometrial receptivity in women suffering from unexplained spontaneous recurrent abortion and/or infertility. The ratio between the levels of expression of the NALP-3 and thrombomodulin proteins in the endometrium is used in the analysis. A ratio of greater than 1 is indicative of an increased condition of endometrial inflammation compared to a fertile subject and is associated with reduced endometrial receptivity.

SUMMARY

It is a general objective to determine EM receptivity status without the need for taking biopsies.

This and other objectives are met by the embodiments.

The present invention is defined in the independent claim. Further embodiments of the invention are defined in the dependent claims.

An aspect of the embodiments relates to a method for determining endometrial (EM) receptivity status of a human female subject. The method comprises measuring, in a uterine fluid (UF) sample taken from the human female subject, a respective amount of at least three proteins selected from the group consisting of nicotinamide N-methyltransferase encoded by the gene NNMT, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNA-SET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2. The method also comprises comparing the respective amount with a respective control amount of the at least three proteins. The method further comprises determining EM receptivity status of the human female subject based on the comparison.

The present invention enables determination of EM receptivity status of a human female subject by measuring proteins present in an UF sample. Hence, no biopsies need to be taken from the human female subject. This means that UF sampling can be performed prior to embryo transfer in the same IVF cycle without any adverse effects on pregnancy rates. The invention provides information of the receptivity status of the endometrium and thereby can be used for determination of the most appropriate day for embryo transfer in an IVF cycle.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
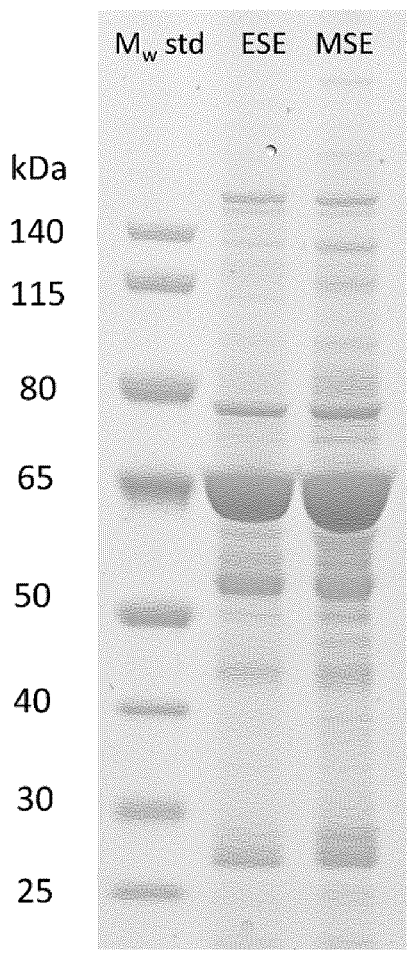
FIG. 1. Uterine fluid contains a high level of serum albumin (band between 60-70 kDa). Sodium dodecyl sulfate-polyacrylamide gel electrophoresis (SDS-PAGE) results are presented for early secretory (ESE) phase and mid-secretory (MSE) phase uterine fluid samples from a healthy fertile woman. Mw std-molecular weight standard.

The present invention generally relates to determination of endometrial receptivity, and in particular to a uterine fluid (UF) protein panel that can be used in such a determination.

The molecular composition of the UF changes across the menstrual cycle. Furthermore, alterations in protein levels in the UF may specifically reflect the receptivity status of the endometrial (EM) tissue. As a consequence, UF proteins can be used in a minimally invasive receptivity test for determination of the most appropriate day for embryo transfer in an in vitro fertilization (IVF) cycle.

Aspiration of UF or uterine lavage is a less invasive approach as compared to taking a tissue sample by biopsy. Furthermore, UF sampling or collection can be performed prior to embryo transfer in the same IVF cycle, without any adverse effect on pregnancy rates. As a consequence, monitoring or determining protein levels in UF would be a highly desired approach for EM receptivity status verification instead of biopsy-based and invasive methods.

An aspect of the embodiments therefore relates to a method for determining EM receptivity status of a human female subject. The method comprises measuring, in a UF sample taken from the human female subject, a respective amount of at least three proteins. The method also comprises comparing the respective amount with a respective control amount of the at least three proteins and determining EM receptivity status of the human female subject based on the comparison. According to the embodiment, the at least three proteins are selected from the group consisting of nicotinamide N-methyltransferase encoded by the gene NNMT, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2.

The endometrial (EM) cycle consists of sequential phase, the proliferative (PE) phase, the secretory phase, including early secretory (ESE) phase and mid-secretory (MSE) phase, and menstruation. Each phase is marked by physiologic changes that are controlled by circulating levels of estrogen and progesterone. Thus, the human endometrium undergoes changes at multiple levels during the menstrual cycle in response to ovarian hormones and paracrine secretions. The endocrine and paracrine secretions control gene expression of the different endometrial cell types. The PE, controlled by estrogen, allows for the proliferation of stromal cells and glands and elongation of the spiral arteries. The postovulatory progesterone rise brings about secretory changes and the endometrium acquires a receptive phenotype permitting implantation of the blastocyst. This period of receptivity is known as the window of implantation (WOI), starting on cycle days 19 or 20 and lasting for about 4-5 days. The WOI coincides with the MSE. Hence, IVF procedure should be scheduled to implant the embryo during WOI and MSE.

EM receptivity as used herein is the state, in which the endometrium is prepared for embryo implantation. As described above, a receptive endometrium corresponds to the WOI, which corresponds to the MSE of the menstrual cycle.

The group of 21 proteins, see Table 7, showed a significant change between ESE phase and MSE phase. Hence, combinations of proteins selected from the group (Table 7) can be used to determine the EM receptivity status of the human female subject and thereby differentiate between the ESE phase, in which the endometrium is in a pre-receptive stage or phase, and the MSE phase, in which the endometrium is in a receptive stage of phase. Hence, in an embodiment, determining EM receptivity status comprises determining whether the human female subject is in an ESE phase or in a MSE phase based on the comparison.

Combinations of the proteins selected from the group (Table 7) can thereby be used to determine whether the endometrium is receptive, i.e., in a receptive stage or phase, or non-receptive, i.e. in a non-receptive stage of phase, such as in a pre-receptive stage or phase. A receptive endometrium as used herein indicates an endometrium that is receptive and prepared for embryo implantation. In an embodiment, determining EM receptivity status therefore comprises determining whether the human female subject has a receptive or a non-receptive endometrium based on the comparison.

Experimental data as presented herein shows that combinations of the proteins selected from the group (Table 7) can not only be used to differentiate between receptive or non-receptive endometrium and ESE or MSE phase but also for distinguishing between normal MSE phase and abnormal MSE phase, such of RIF women. In more detail, combinations of proteins selected from the group (Table 7) were able to differentiate, at high specificity and sensitivity, between normal or healthy MSE phase and RIF MSE phase. This means that the combinations of proteins selected from the group (Table 7) can be used, in an embodiment of determining EM receptivity status, to determine whether the human female subject is in a MSE phase or a RIF MSE phase based on the comparison.

Experimental data as shown herein indicates that RIF women had an MSE molecular signature with regard to protein levels in the UF reminiscent of a pre-receptive phase or ESE phase as seen in UF samples from control women taken during the ESE phase. Hence, if a woman has had multiple failed IVF cycles and the combination of proteins selected from the group (Table 7) and measured in an UF sample taken from the woman indicates protein levels corresponding to ESE phase although the woman is in the MSE phase, then the woman could be diagnosed with a RIF caused by a shifted development of the endometrium. For such a woman, a different time point could be tried for embryo transfer.

Hence, combinations or panels of proteins selected from the group (Table 7) and measured in a UF sample constitute a valuable diagnostic tool in IVF by identifying the EM receptivity status of human female subjects undergoing IVF procedure, and in particular using the UF protein panels in determining whether the endometrium of the human female subject is in the MSE phase and thereby being receptive and/or in identifying human female subjects suffering from RIF.

The group of proteins as listed in Table 7 are all present in the uterine fluid and the levels or amounts thereof can be measured in an UF sample. The UF sample can be obtained according to any known technique or method for UF sampling. For instance, the UF sample can be obtained by aspiration. As an example, an intrauterine catheter, such as an intrauterine insemination catheter, may be inserted through the cervical canal into the uterine cavity to aspirate the uterine fluid. In an embodiment, the method therefore comprises collecting the UF sample from the human female subject. This UF sample collection may be performed by aspirating uterine fluid from the uterine cavity of the human female subject, such as by using an intrauterine catheter inserted through the cervical canal into the uterine cavity.

In an embodiment, the uterine fluid is obtained by lavage after flushing the uterus with water or an aqueous solution, such as phosphate buffered saline (PBS). In such an embodiment, the method also comprises flushing the uterus of the human female subject with water or an aqueous solution prior to collecting the UF sample, such as by aspiration.

Combinations of proteins selected from the group shown in Table 7 have very high sensitivity ($\geq 0.9$) and specificity ($\geq 0.9$) and thereby a combined sensitivity and specificity of at least 1.8. Sensitivity as used herein indicates the fraction of human female subjects with RIF who tests positive for RIF MSE phase or the fraction of human female subjects being in the MSE phase who tests positive for MSE phase endometrium. Correspondingly, specificity indicates the fraction of female subjects without RIF who tests negative for RIF MSE phase (normal MSE phase) or the fraction of human female subjects in the ESE phase who tests negative for MSE phase endometrium.

Herein follows a brief description of the proteins in Table 7.

Nicotinamide N-methyltransferase (NNMT) (EC 2.1.1.1) is an enzyme that catalyzes the chemical reaction S-adenosyl-L-methionine+nicotinamide⇌S-adenosyl-L-homocysteine+1-methylnicotinamide. This enzyme participates in nicotinate and nicotinamide metabolism. NNMT affects a biochemical mechanism known as a futile cycle, which plays a role in metabolic regulation. NNMT is found in human fat cells and the liver. NNMT processes vitamin B3.

Transcobalamin-1 (TCN1), also known as haptocorrin, R-factor, and R-protein, is a glycoprotein produced by the salivary glands of the mouth. It primarily serves to protect cobalamin (vitamin B12) from acid degradation in the stomach by producing a TCN1-vitamin B12 complex. Once the complex has traveled to the more neutral duodenum, pancreatic proteases degrade TCN1, releasing free cobalamin, which now binds to intrinsic factor for absorption by ileal enterocytes.

SLC26A2 protein, also referred to as diastrophic dysplasia sulfate transporter (DTDST), is a member of the solute carrier family. This sulfate ($SO_4^{2-}$) transporter also accepts chloride, hydroxyl ions ($OH^-$), and oxalate as substrates. In chondrocytes, SLC26A2 functions to transport most of the cellular sulfate, which is critical for the sulfation of proteoglycans and normal cartilage formation. In addition, SLC26A2 influences chondrocyte proliferation, differentiation, and growth, suggesting that in the chondrocyte, SLC26A2 provides sulfate for both structural and regulatory proteins.

Ectonucleotide pyrophosphatase/phosphodiesterase family member 3 (ENPP3) belongs to a series of ectoenzymes (EC 3.6.1.9) that are involved in hydrolysis of extracellular nucleotides. These ectoenzymes possess ATPase and ATP pyrophosphatase activities and are type II transmembrane proteins. Expression of the ENPP3 protein has been detected in uterus, basophils, and mast cells.

Granulin (GRN) is cleaved from the precursor progranulin, a 593 amino acid long and 68.5 kDa protein. While the function of progranulin and granulin have yet to be determined, both forms of the protein have been implicated in development, inflammation, cell proliferation and protein homeostasis.

Stanniocalcin, also referred to as hypocalcin, teleocalcin or parathyrin, is a family of hormones which regulate calcium and phosphate balance in the body. Chemically, stanniocalcins are glycosylated proteins having a molecular mass of 50 kDa. They exist in molecular pairs (homodimers) and are joined together by disulfide linkage. In mammals, the predominant function of STC1 is to activate phosphate reabsorption in the small intestine and proximal tubules of the kidney.

Dipeptidyl peptidase-4 (DPP4), also known as adenosine deaminase complexing protein 2 or cluster of differentiation 26 (CD26), is an enzyme (EC 3.4.14.5) expressed on the surface of most cell types and is associated with immune regulation, signal transduction, and apoptosis. It is a type II transmembrane glycoprotein, but a soluble form, which lacks the intracellular and transmembrane part, is present in blood plasma and various body fluids. DPP-4 is a serine exopeptidase that cleaves X-proline or X-alanine dipeptides from the N-terminus of polypeptides. DPP-4 is known to cleave a broad range of substrates including growth factors, chemokines, neuropeptides, and vasoactive peptides.

Myeloperoxidase (MPO) is a peroxidase enzyme (EC 1.11.2.2) that is most abundantly expressed in neutrophil granulocytes and produces hypohalous acids to carry out their antimicrobial activity. It is a lysosomal protein stored in azurophilic granules of the neutrophil and released into the extracellular space during degranulation. Neutrophil myeloperoxidase has a heme pigment, which causes its green color in secretions rich in neutrophils, such as pus and some forms of mucus.

Complement decay-accelerating factor, also known as CD55 or DAF, regulates the complement system on the cell surface. It recognizes C4b and C3b fragments that are created during activation of C4 (classical or lectin pathway) or C3 (alternative pathway). Interaction of CD55 with cell-associated C4b of the classical and lectin pathways interferes with the conversion of C2 to C2b, thereby preventing formation of the C4b2b C3-convertase, and interaction of CD55 with C3b of the alternative pathway interferes with the conversion of factor B to Bb by factor D, thereby preventing formation of the C3bBb C3 convertase of the alternative pathway. Thus, by limiting the amplification convertases of the complement cascade, CD55 indirectly blocks the formation of the membrane attack complex.

Neutrophil elastase (ELANE), also referred to as leukocyte elastase, elastase 2 (ELA2), is a serine proteinase (EC 3.4.21.37) in the same family as chymotrypsin and has broad substrate specificity. Secreted by neutrophils and macrophages during inflammation, it destroys bacteria and host tissue. It also localizes to neutrophil extracellular traps (NETs), via its high affinity for DNA.

Sodium-dependent phosphate transport protein 2B (SLC34A2), also referred to as NaPi2b, is a tumor-associated antigen.

Lipocalin-2 (LCN2), also known as oncogene 24p3 or neutrophil gelatinase-associated lipocalin (NGAL), is involved in innate immunity by sequestrating iron that in turn limits bacterial growth. It is expressed in neutrophils and in low levels in the kidney, prostate, and epithelia of the respiratory and alimentary tracts. The binding of LCN2 to bacterial siderophores is important in the innate immune response to bacterial infection. Upon encountering invading bacteria the toll-like receptors on immune cells stimulate the synthesis and secretion of LCN2. Secreted LCN2 then limits bacterial growth by sequestering iron-containing siderophores. LCN2 also binds to the mammalian siderophore 2,5-dihydroxybenzoic acid (2,5-DHBA). This complex ensures that excess free iron does not accumulate in the cytoplasm.

Mesothelin (MSLN) is a 40 kDa protein that is expressed in mesothelial cells. Although it has been proposed that mesothelin may be involved in cell adhesion, its biological function is not known.

Cathepsin B (CTSB) belongs to a family of lysosomal cysteine proteases (EC 3.4.22.1) and plays an important role in intracellular proteolysis. Cathepsin B may enhance the activity of other protease, including matrix metalloproteinase, urokinase, and cathepsin D, and, thus, it has an essential position for in the proteolysis of extracellular matrix components, intercellular communication disruption, and reduced protease inhibitor expression.

Ribonuclease T2 (RNASET2) is an enzyme (EC 3.1.27.1) that catalyzes the two-stage endonucleolytic cleavage to nucleoside 3'-phosphates and 3'-phosphooligonucleotides with 2',3'-cyclic phosphate intermediates.

Cysteine-rich secretory protein 3 (CRISP3) is a cysteine-rich secretory protein, which is a group of glycoproteins substantially implicated in the functioning of the mammalian reproductive system.

Major vault protein (MVP) are assembled into large compartments called vaults. Vaults are multi-subunit structures that may be involved in nucleo-cytoplasmic transport. This protein mediates drug resistance, perhaps via a transport process. It is widely distributed in normal tissues, and overexpressed in multidrug-resistant cancer cells.

Matrix metalloproteinase-26 (MMP26), also known as matrilysin-2 and endometase, is an enzyme (EC 3.4.24.-) of the matrix metalloproteinase (MMP) family, which are involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. The encoded protein degrades type IV collagen, fibronectin, fibrinogen, casein, vitronectin, alpha 1-antitrypsin (A1AT), alpha 2-macroglobulin (A2M), and insulin-like growth factor-binding protein 1 (IGFBP), and activates MMP9 by cleavage. The MMP26 protein differs from most MMP family members in that it lacks a conserved C-terminal protein domain.

Amine oxidase (copper-containing) (AOC) (EC 1.4.3.21 and EC 1.4.3.22; formerly EC 1.4.3.6) is a family of amine oxidase enzymes, which includes both primary-amine oxidase and diamine oxidase. These enzymes catalyze the oxidation of a wide range of biogenic amines including many neurotransmitters, histamine and xenobiotic amines. They act as a disulphide-linked homodimer. They catalyze the oxidation of primary amines to aldehydes, with the subsequent release of ammonia and hydrogen peroxide, which requires one copper ion per subunit and topaquinone as cofactor.

Diamine oxidase (DAO), also known as histaminase, is an enzyme (EC 1.4.3.22) is an AOC encoded by the AOC1 gene in humans and is involved in the metabolism, oxidation, and inactivation of histamine and other polyamines, such as putrescine or spermidine. In humans, a certain subtype of cells of the placenta, namely the extravillous trophoblasts, express the enzyme and secrete it into the blood stream of a pregnant woman. Lowered diamine oxidase values in maternal blood in early pregnancy might be an indication for trophoblast-related pregnancy disorders like early-onset preeclampsia.

Syntenin-2 is a protein that in humans is encoded by the SDCBP2 gene.

Progesterone receptor (PGR or PR), also known as nuclear receptor subfamily 3, group C, member 3 (NR3C3), is a protein found inside cells. It is activated by the steroid hormone progesterone. Progesterone is necessary to induce the progesterone receptors. When no binding hormone is present the carboxyl terminal inhibits transcription. Binding to a hormone induces a structural change that removes the achieve sufficiently high sensitivity and specificity. A higher combined sensitivity may be obtained with a four UF protein panel. Increasing the number of the proteins in the UF protein panel, e.g., five or six proteins, generally does not significantly increase the combined sensitivity and specificity, or at least does not lead to an increased combined sensitivity and specificity that compensates for the extra work and effort of measuring one or two proteins more than four proteins. Although a protein panel of at least three proteins and no more than six proteins is generally preferred, the embodiments are not limited thereto and more than six proteins out of the group in Table 7 could be measured, such as 7, 8, 9, 10, 11, 12, 13, 14, 15, 16, 17, 18, 19, 20 or all 21 proteins.

In a preferred embodiment, the method thereby comprises measuring, in the UF sample taken from the human female subject, the respective amount of at least three but no more than six proteins selected from the group. The method also comprises comparing the respective amount with the respective control amount of the at least three but no more than six proteins.

Table 1 below shows currently preferred UF protein panels of three proteins together with sensitivity and specificity values. Combined as shown in Table 1 and also in Tables 2 to 4 indicates combined sensitivity and specificity, i.e., combined=sensitivity+specificity.

TABLE 1

| | 3 protein panels | | | | | |
| | MSE vs. MSE RIF | | | ESE vs. MSE | | |
| Proteins | sensitivity | specificity | combined | sensitivity | specificity | combined |
|---|---|---|---|---|---|---|
| ELANE NNMT SLC26A2 | 0.931 | 0.917 | 1.848 | 0.917 | 1.000 | 1.917 |
| CD55 CTSB NNMT | 0.966 | 0.917 | 1.882 | 0.917 | 0.917 | 1.833 |
| CTSB NNMT STC1 | 0.966 | 0.917 | 1.882 | 1.000 | 0.833 | 1.833 | inhibitory action. Progesterone antagonists prevent the structural reconfiguration. After progesterone binds to the receptor, restructuring with dimerization follows and the complex enters the nucleus and binds to DNA. There transcription takes place, resulting in formation of messenger RNA that is translated by ribosomes to produce specific proteins.

As described in the foregoing, the method comprises measuring a respective amount of at least three proteins in the UF sample taken from the human female subject. Hence, the UF protein panel comprises at least three proteins. In an embodiment, the UF protein panel comprises three proteins. In another embodiment, the UF protein panel comprises four proteins. In a further embodiment, the UF protein panel comprises five proteins. In yet another embodiment, the UF protein panel comprises six proteins. Hence, in an embodiment, the method comprises measuring a respective amount of at least three proteins but no more than six proteins in the UF sample taken from the human female subject, such as measuring a respective amount of three proteins, of four proteins, of five proteins or of six proteins in the UF sample taken form the human female subject.

Experimental data as presented herein indicates that at least three proteins should be measured in the UF sample to In an embodiment, measuring the respective amount comprises measuring, in the UF sample taken from the human female subject, a respective amount of NNMT and at least two proteins selected from the group consisting of ELANE, SLC26A2, CD55, CTSB and STC1. In another embodiment, measuring the respective amount comprises measuring, in the UF sample taken from the human female subject, a respective amount of NNMT, CTSB and at least one protein selected from the group consisting of CD55 and STC1.

In an embodiment, measuring the respective amount comprises measuring, in the UF sample taken from the human female subject, a respective amount of ELANE, NNMT and SLC26A2; a respective amount of CD55, CTSB and NNMT; or a respective amount of CTSB, NNMT and STC1.

Table 2 below shows the corresponding preferred UF protein panels of four proteins together with sensitivity and specificity values.

TABLE 2

| | 4 protein panels | | | | | |
|---|---|---|---|---|---|---|
| | MSE vs. MSE RIF | | | ESE vs. MSE | | |
| Proteins | sensitivity | specificity | combined | sensitivity | specificity | combined |
| CD55<br>CTSB<br>MSLN<br>NNMT | 0.931 | 0.917 | 1.848 | 0.917 | 0.917 | 1.833 |
| DPP4<br>LCN2<br>NNMT<br>PGR | 0.931 | 0.917 | 1.848 | 0.917 | 0.917 | 1.833 |
| LCN2<br>NNMT<br>PGR<br>SLC26A2 | 0.966 | 0.917 | 1.882 | 0.917 | 0.917 | 1.833 |
| LCN2<br>NNMT<br>PGR<br>SLC34A2 | 0.931 | 0.917 | 1.848 | 0.917 | 0.917 | 1.833 |

In an embodiment, measuring the respective amount comprises measuring, in the UF sample taken from the human female subject, a respective amount of NNMT and at least three proteins selected from the group consisting of CD55, CTSB, MSLN, DPP4, LCN2, PGR, SLC26A2 and SLC34A2. In another embodiment, measuring the respective amount comprises measuring, in the UF sample taken from the human female subject, a respective amount of NNMT, LCN2, PGR and at least one protein selected from the group consisting DPP4, SLC26A2 and SLC34A2.

In an embodiment, measuring the respective amount comprises measuring, in the UF sample taken from the human female subject, a respective amount of CD55, CTSB, MSLN and NNMT; a respective amount of DPP4, LCN2, NNMT and PGR; a respective amount of LCN2, NNMT, PGR and SLC26A2; or a respective amount of LCN2, NNMT, PGR and SLC34A2.

Table 3 below shows the corresponding preferred UF protein panels of five proteins together with combined values.

TABLE 3

| | | | | | Combined MSE vs. MSE RIF | Combined ESE vs. MSE |
|---|---|---|---|---|---|---|
| | | Proteins | | | | |
| CRISP3 | CTSB | MVP | NNMT | STC1 | 1.882 | 1.917 |
| CTSB | ELANE | NNMT | SLC26A2 | SLC34A2 | 1.966 | 1.917 |
| AOC1 | CD55 | CTSB | MMP26 | NNMT | 1.882 | 1.833 |
| AOC1 | CD55 | CTSB | MSLN | NNMT | 1.848 | 1.833 |
| CD55 | CTSB | ENPP3 | NNMT | TCN1 | 1.882 | 1.833 |
| CD55 | CTSB | GRN | NNMT | STC1 | 1.882 | 1.833 |
| CD55 | CTSB | LCN2 | MPO | NNMT | 1.882 | 1.833 |
| CD55 | CTSB | NNMT | SLC26A2 | TCN1 | 1.882 | 1.833 |
| CRISP3 | CTSB | MVP | NNMT | TCN1 | 1.882 | 1.833 |
| CRISP3 | LCN2 | NNMT | PGR | SLC26A2 | 1.848 | 1.833 |
| CRISP3 | LCN2 | NNMT | PGR | SLC34A2 | 1.848 | 1.833 |
| CTSB | DPP4 | ENPP3 | LCN2 | NNMT | 1.882 | 1.833 |
| CTSB | DPP4 | LCN2 | MMP26 | NNMT | 1.882 | 1.833 |
| CTSB | DPP4 | LCN2 | NNMT | PGR | 1.882 | 1.833 |
| CTSB | GRN | MMP26 | NNMT | STC1 | 1.882 | 1.833 |
| CTSB | MPO | NNMT | SLC26A2 | TCN1 | 1.882 | 1.833 |
| CTSB | MVP | NNMT | PGR | STC1 | 1.882 | 1.833 |
| DPP4 | LCN2 | NNMT | PGR | RNASET2 | 1.848 | 1.833 |
| ELANE | MVP | NNMT | PGR | SLC26A2 | 1.882 | 1.833 |
| LCN2 | MMP26 | NNMT | PGR | SLC34A2 | 1.882 | 1.833 |
| LCN2 | MSLN | NNMT | PGR | SLC26A2 | 1.882 | 1.833 |
| LCN2 | MSLN | NNMT | PGR | SLC34A2 | 1.882 | 1.833 |
| AOC1 | CTSB | LCN2 | NNMT | STC1 | 1.882 | 1.833 |
| AOC1 | LCN2 | NNMT | PGR | SLC26A2 | 1.848 | 1.833 |
| CD55 | ELANE | ENPP3 | NNMT | PGR | 1.882 | 1.833 |
| CD55 | ELANE | NNMT | PGR | SLC26A2 | 1.882 | 1.833 |
| CD55 | ELANE | NNMT | PGR | SLC34A2 | 1.882 | 1.833 |
| CD55 | ELANE | NNMT | PGR | STC1 | 1.848 | 1.833 |
| CRISP3 | CTSB | ENPP3 | NNMT | STC1 | 1.848 | 1.833 |
| CRISP3 | CTSB | LCN2 | NNMT | STC1 | 1.882 | 1.833 |
| CTSB | ELANE | MMP26 | NNMT | PGR | 1.882 | 1.833 |
| CTSB | ELANE | MSLN | NNMT | SLC26A2 | 1.931 | 1.833 |
| CTSB | ELANE | NNMT | PGR | SLC26A2 | 1.882 | 1.833 |
| CTSB | ENPP3 | LCN2 | NNMT | STC1 | 1.882 | 1.833 |

TABLE 3-continued

| | | 5 protein panels | | | | |
|---|---|---|---|---|---|---|
| | | Proteins | | | Combined MSE vs. MSE RIF | Combined ESE vs. MSE |
| CTSB | ENPP3 | NNMT | PGR | STC1 | 1.882 | 1.833 |
| CTSB | ENPP3 | NNMT | RNASET2 | STC1 | 1.848 | 1.833 |
| CTSB | LCN2 | MMP26 | NNMT | STC1 | 1.882 | 1.833 |
| CTSB | LCN2 | NNMT | PGR | STC1 | 1.882 | 1.833 |
| CTSB | LCN2 | NNMT | RNASET2 | SLC26A2 | 1.882 | 1.833 |
| CTSB | LCN2 | NNMT | RNASET2 | STC1 | 1.882 | 1.833 |
| CTSB | NNMT | PGR | SLC26A2 | TCN1 | 1.882 | 1.833 |
| ELANE | GRN | NNMT | PGR | SDCBP2 | 1.882 | 1.833 |
| ENPP3 | LCN2 | MMP26 | NNMT | PGR | 1.848 | 1.833 |
| GRN | LCN2 | MVP | NNMT | PGR | 1.848 | 1.833 |
| LCN2 | MMP26 | NNMT | PGR | STC1 | 1.848 | 1.833 |
| LCN2 | MSLN | NNMT | PGR | STC1 | 1.848 | 1.833 |
| LCN2 | MVP | NNMT | PGR | STC1 | 1.848 | 1.833 |
| LCN2 | NNMT | PGR | RNASET2 | STC1 | 1.848 | 1.833 |
| LCN2 | NNMT | PGR | SLC34A2 | STC1 | 1.848 | 1.833 |

In an embodiment, measuring the respective amount comprises measuring, in the UF sample taken from the human female subject, a respective amount of five proteins as listed in any of the UF protein panels shown in Table 3.

Table 4 below shows the corresponding preferred UF protein panels of six proteins together with combined values.

TABLE 4

| | | | 6 protein panels | | | | |
|---|---|---|---|---|---|---|---|
| | | | Proteins | | | Combined MSE vs. MSE RIF | Combined ESE vs. MSE |
| AOC1 | ENPP3 | LCN2 | NNMT | PGR | SLC26A2 | 1.848 | 1.917 |
| CD55 | CTSB | ELANE | MVP | NNMT | SLC26A2 | 1.848 | 1.917 |
| CD55 | CTSB | ELANE | NNMT | PGR | SDCBP2 | 1.882 | 1.917 |
| CD55 | CTSB | MSLN | MVP | NNMT | STC1 | 1.848 | 1.917 |
| CD55 | ELANE | MVP | NNMT | PGR | SLC26A2 | 1.882 | 1.917 |
| CD55 | ELANE | NNMT | PGR | SDCBP2 | SLC34A2 | 1.882 | 1.917 |
| CRISP3 | CTSB | ELANE | NNMT | SLC26A2 | SLC34A2 | 1.882 | 1.917 |
| CRISP3 | CTSB | MVP | NNMT | STC1 | TCN1 | 1.848 | 1.917 |
| CTSB | ELANE | MVP | NNMT | SLC26A2 | STC1 | 1.882 | 1.917 |
| CTSB | ELANE | NNMT | RNASET2 | SLC26A2 | SLC34A2 | 1.882 | 1.917 |
| CTSB | ELANE | NNMT | SDCBP2 | SLC26A2 | TCN1 | 1.848 | 1.917 |
| ELANE | GRN | MVP | NNMT | PGR | SLC26A2 | 1.882 | 1.917 |
| AOC1 | CD55 | CTSB | DPP4 | ENPP3 | NNMT | 1.882 | 1.833 |
| AOC1 | CD55 | CTSB | ELANE | NNMT | SLC26A2 | 1.882 | 1.833 |
| AOC1 | CD55 | CTSB | ENPP3 | NNMT | TCN1 | 1.848 | 1.833 |
| AOC1 | CD55 | CTSB | NNMT | SLC26A2 | TCN1 | 1.882 | 1.833 |
| AOC1 | CD55 | CTSB | NNMT | SLC34A2 | STC1 | 1.882 | 1.833 |
| AOC1 | CRISP3 | CTSB | ELANE | NNMT | SLC26A2 | 1.966 | 1.833 |
| AOC1 | CRISP3 | CTSB | NNMT | SLC26A2 | TCN1 | 1.848 | 1.833 |
| AOC1 | CTSB | DPP4 | LCN2 | NNMT | SLC26A2 | 1.848 | 1.833 |
| AOC1 | CTSB | DPP4 | NNMT | SDCBP2 | STC1 | 1.882 | 1.833 |
| AOC1 | CTSB | ELANE | ENPP3 | NNMT | SLC26A2 | 1.931 | 1.833 |
| AOC1 | CTSB | ELANE | MMP26 | NNMT | SLC26A2 | 1.966 | 1.833 |
| AOC1 | CTSB | ELANE | MSLN | NNMT | SLC26A2 | 1.848 | 1.833 |
| AOC1 | CTSB | ELANE | NNMT | PGR | SDCBP2 | 1.882 | 1.833 |
| AOC1 | CTSB | ELANE | NNMT | SLC26A2 | SLC34A2 | 1.966 | 1.833 |
| AOC1 | CTSB | MVP | NNMT | PGR | STC1 | 1.882 | 1.833 |
| CD55 | CRISP3 | CTSB | GRN | NNMT | STC1 | 1.848 | 1.833 |
| CD55 | CRISP3 | CTSB | MVP | NNMT | STC1 | 1.882 | 1.833 |
| CD55 | CRISP3 | CTSB | NNMT | SLC26A2 | TCN1 | 1.848 | 1.833 |
| CD55 | CTSB | DPP4 | ELANE | NNMT | SLC26A2 | 1.882 | 1.833 |
| CD55 | CTSB | ENPP3 | GRN | NNMT | TCN1 | 1.848 | 1.833 |
| CD55 | CTSB | ENPP3 | MSLN | NNMT | TCN1 | 1.848 | 1.833 |
| CD55 | CTSB | ENPP3 | NNMT | SLC26A2 | TCN1 | 1.813 | 1.833 |
| CD55 | CTSB | ENPP3 | NNMT | SLC34A2 | TCN1 | 1.882 | 1.833 |
| CD55 | CTSB | GRN | MSLN | NNMT | STC1 | 1.848 | 1.833 |
| CD55 | CTSB | MMP26 | NNMT | SLC34A2 | TCN1 | 1.882 | 1.833 |
| CD55 | CTSB | MSLN | NNMT | SLC34A2 | STC1 | 1.848 | 1.833 |
| CD55 | MMP26 | NNMT | SDCBP2 | SLC26A2 | STC1 | 1.813 | 1.833 |
| CRISP3 | CTSB | DPP4 | LCN2 | NNMT | SLC26A2 | 1.848 | 1.833 |

TABLE 4-continued

| | | | | | | Combined MSE vs. MSE RIF | Combined ESE vs. MSE |
|---|---|---|---|---|---|---|---|
| | 6 protein panels |

| | | | Proteins | | | Combined MSE vs. MSE RIF | Combined ESE vs. MSE |
|---|---|---|---|---|---|---|---|
| CRISP3 | CTSB | DPP4 | NNMT | SDCBP2 | TCN1 | 1.848 | 1.833 |
| CRISP3 | CTSB | ELANE | MVP | NNMT | SLC26A2 | 1.966 | 1.833 |
| CRISP3 | CTSB | MMP26 | MPO | MSLN | NNMT | 1.882 | 1.833 |
| CRISP3 | CTSB | MVP | NNMT | PGR | STC1 | 1.882 | 1.833 |
| CRISP3 | CTSB | MVP | NNMT | PGR | TCN1 | 1.882 | 1.833 |
| CRISP3 | LCN2 | MMP26 | NNMT | PGR | SLC34A2 | 1.848 | 1.833 |
| CTSB | DPP4 | ELANE | ENPP3 | NNMT | SLC26A2 | 1.966 | 1.833 |
| CTSB | DPP4 | ELANE | GRN | NNMT | PGR | 1.882 | 1.833 |
| CTSB | DPP4 | ELANE | LCN2 | MVP | NNMT | 1.882 | 1.833 |
| CTSB | DPP4 | ELANE | LCN2 | NNMT | SLC34A2 | 1.882 | 1.833 |
| CTSB | DPP4 | ELANE | NNMT | PGR | SLC26A2 | 1.966 | 1.833 |
| CTSB | DPP4 | ELANE | NNMT | SLC26A2 | SLC34A2 | 1.966 | 1.833 |
| CTSB | DPP4 | ELANE | PGR | SDCBP2 | TCN1 | 1.882 | 1.833 |
| CTSB | DPP4 | ELANE | SDCBP2 | SLC26A2 | STC1 | 1.882 | 1.833 |
| CTSB | ELANE | ENPP3 | MMP26 | MVP | NNMT | 1.882 | 1.833 |
| CTSB | ELANE | GRN | NNMT | SLC26A2 | SLC34A2 | 1.966 | 1.833 |
| CTSB | ELANE | MMP26 | MSLN | NNMT | SLC26A2 | 1.848 | 1.833 |
| CTSB | ELANE | MMP26 | NNMT | PGR | SDCBP2 | 1.882 | 1.833 |
| CTSB | ELANE | MVP | NNMT | SLC26A2 | TCN1 | 1.882 | 1.833 |
| CTSB | ENPP3 | MPO | NNMT | SLC26A2 | TCN1 | 1.882 | 1.833 |
| CTSB | ENPP3 | MVP | NNMT | PGR | STC1 | 1.882 | 1.833 |
| CTSB | MMP26 | MVP | NNMT | PGR | STC1 | 1.882 | 1.833 |
| CTSB | MPO | NNMT | SLC26A2 | SLC34A2 | TCN1 | 1.882 | 1.833 |
| CTSB | MVP | NNMT | PGR | RNASET2 | STC1 | 1.882 | 1.833 |
| CTSB | MVP | NNMT | PGR | RNASET2 | TCN1 | 1.882 | 1.833 |
| CTSB | MVP | NNMT | PGR | SLC26A2 | STC1 | 1.882 | 1.833 |
| CTSB | MVP | NNMT | PGR | SLC26A2 | TCN1 | 1.882 | 1.833 |
| CTSB | MVP | NNMT | PGR | SLC34A2 | STC1 | 1.882 | 1.833 |
| CTSB | MVP | NNMT | PGR | SLC34A2 | TCN1 | 1.882 | 1.833 |
| CTSB | NNMT | PGR | RNASET2 | SLC26A2 | TCN1 | 1.848 | 1.833 |
| ELANE | NNMT | PGR | SDCBP2 | SLC26A2 | TCN1 | 1.848 | 1.833 |
| MPO | MVP | NNMT | PGR | SLC26A2 | STC1 | 1.833 | 1.833 |
| AOC1 | CTSB | ELANE | ENPP3 | NNMT | SDCBP2 | 1.882 | 1.833 |
| AOC1 | CTSB | ELANE | LCN2 | NNMT | SDCBP2 | 1.882 | 1.833 |
| AOC1 | CTSB | ELANE | NNMT | SLC26A2 | STC1 | 1.882 | 1.833 |
| AOC1 | CTSB | ENPP3 | LCN2 | NNMT | SLC34A2 | 1.882 | 1.833 |
| AOC1 | CTSB | ENPP3 | LCN2 | NNMT | STC1 | 1.882 | 1.833 |
| AOC1 | CTSB | LCN2 | MSLN | NNMT | STC1 | 1.848 | 1.833 |
| AOC1 | CTSB | LCN2 | NNMT | PGR | STC1 | 1.882 | 1.833 |
| AOC1 | CTSB | LCN2 | NNMT | RNASET2 | STC1 | 1.882 | 1.833 |
| AOC1 | CTSB | NNMT | PGR | SLC26A2 | STC1 | 1.882 | 1.833 |
| AOC1 | ENPP3 | LCN2 | NNMT | PGR | STC1 | 1.848 | 1.833 |
| CD55 | CRISP3 | CTSB | ELANE | LCN2 | NNMT | 1.848 | 1.833 |
| CD55 | CRISP3 | CTSB | ELANE | LCN2 | STC1 | 1.882 | 1.833 |
| CD55 | CRISP3 | CTSB | ELANE | PGR | STC1 | 1.882 | 1.833 |
| CD55 | CTSB | ELANE | ENPP3 | LCN2 | NNMT | 1.848 | 1.833 |
| CD55 | CTSB | ELANE | ENPP3 | NNMT | SLC26A2 | 1.848 | 1.833 |
| CD55 | CTSB | ELANE | ENPP3 | NNMT | STC1 | 1.882 | 1.833 |
| CD55 | CTSB | ELANE | ENPP3 | PGR | STC1 | 1.882 | 1.833 |
| CD55 | CTSB | ELANE | LCN2 | NNMT | SDCBP2 | 1.848 | 1.833 |
| CD55 | CTSB | ELANE | MSLN | RNASET2 | STC1 | 1.848 | 1.833 |
| CD55 | CTSB | ELANE | NNMT | PGR | STC1 | 1.882 | 1.833 |
| CD55 | CTSB | LCN2 | MVP | NNMT | SLC26A2 | 1.848 | 1.833 |
| CRISP3 | CTSB | ELANE | ENPP3 | NNMT | SDCBP2 | 1.848 | 1.833 |
| CRISP3 | CTSB | ELANE | ENPP3 | NNMT | SLC26A2 | 1.882 | 1.833 |
| CRISP3 | CTSB | ELANE | ENPP3 | NNMT | SLC34A2 | 1.882 | 1.833 |
| CRISP3 | CTSB | ELANE | GRN | PGR | STC1 | 1.882 | 1.833 |
| CRISP3 | CTSB | ELANE | MMP26 | NNMT | SDCBP2 | 1.882 | 1.833 |
| CRISP3 | CTSB | ELANE | MMP26 | NNMT | STC1 | 1.882 | 1.833 |
| CRISP3 | CTSB | ELANE | MSLN | NNMT | SLC26A2 | 1.848 | 1.833 |
| CRISP3 | CTSB | ELANE | NNMT | PGR | SLC26A2 | 1.882 | 1.833 |
| CRISP3 | CTSB | ELANE | NNMT | SDCBP2 | SLC34A2 | 1.882 | 1.833 |
| CRISP3 | CTSB | ELANE | NNMT | SLC26A2 | TCN1 | 1.931 | 1.833 |
| CRISP3 | CTSB | ENPP3 | LCN2 | NNMT | STC1 | 1.848 | 1.833 |
| CRISP3 | CTSB | ENPP3 | NNMT | PGR | SLC26A2 | 1.848 | 1.833 |
| CRISP3 | CTSB | ENPP3 | NNMT | PGR | STC1 | 1.882 | 1.833 |
| CRISP3 | CTSB | LCN2 | MMP26 | NNMT | STC1 | 1.882 | 1.833 |
| CRISP3 | CTSB | LCN2 | NNMT | PGR | STC1 | 1.882 | 1.833 |
| CRISP3 | CTSB | LCN2 | NNMT | RNASET2 | SLC26A2 | 1.848 | 1.833 |
| CRISP3 | CTSB | LCN2 | NNMT | RNASET2 | STC1 | 1.848 | 1.833 |
| CRISP3 | ENPP3 | LCN2 | MMP26 | NNMT | PGR | 1.848 | 1.833 |
| CRISP3 | LCN2 | MMP26 | NNMT | PGR | STC1 | 1.848 | 1.833 |
| CRISP3 | LCN2 | MSLN | NNMT | PGR | STC1 | 1.848 | 1.833 |
| CRISP3 | LCN2 | MVP | NNMT | PGR | STC1 | 1.848 | 1.833 |
| CRISP3 | LCN2 | NNMT | PGR | RNASET2 | STC1 | 1.848 | 1.833 |

TABLE 4-continued

| | | | | | | Combined MSE vs. MSE RIF | Combined ESE vs. MSE |
|---|---|---|---|---|---|---|---|
| | | | 6 protein panels | | | | |
| | | | Proteins | | | | |
| CRISP3 | LCN2 | NNMT | PGR | SLC34A2 | STC1 | 1.848 | 1.833 |
| CTSB | DPP4 | ELANE | ENPP3 | NNMT | PGR | 1.882 | 1.833 |
| CTSB | DPP4 | ELANE | LCN2 | NNMT | SDCBP2 | 1.882 | 1.833 |
| CTSB | DPP4 | ELANE | NNMT | SDCBP2 | SLC26A2 | 1.882 | 1.833 |
| CTSB | ELANE | ENPP3 | GRN | NNMT | SDCBP2 | 1.882 | 1.833 |
| CTSB | ELANE | ENPP3 | GRN | NNMT | STC1 | 1.882 | 1.833 |
| CTSB | ELANE | ENPP3 | GRN | PGR | STC1 | 1.882 | 1.833 |
| CTSB | ELANE | ENPP3 | LCN2 | NNMT | STC1 | 1.882 | 1.833 |
| CTSB | ELANE | ENPP3 | LCN2 | NNMT | TCN1 | 1.882 | 1.833 |
| CTSB | ELANE | ENPP3 | MMP26 | NNMT | SDCBP2 | 1.882 | 1.833 |
| CTSB | ELANE | ENPP3 | MMP26 | NNMT | SLC34A2 | 1.882 | 1.833 |
| CTSB | ELANE | ENPP3 | MMP26 | NNMT | STC1 | 1.882 | 1.833 |
| CTSB | ELANE | ENPP3 | MSLN | NNMT | SLC26A2 | 1.931 | 1.833 |
| CTSB | ELANE | ENPP3 | NNMT | PGR | STC1 | 1.882 | 1.833 |
| CTSB | ELANE | ENPP3 | NNMT | PGR | TCN1 | 1.882 | 1.833 |
| CTSB | ELANE | ENPP3 | NNMT | SDCBP2 | SLC34A2 | 1.882 | 1.833 |
| CTSB | ELANE | ENPP3 | NNMT | SDCBP2 | STC1 | 1.882 | 1.833 |
| CTSB | ELANE | ENPP3 | NNMT | SLC26A2 | SLC34A2 | 1.931 | 1.833 |
| CTSB | ELANE | ENPP3 | NNMT | SLC26A2 | TCN1 | 1.931 | 1.833 |
| CTSB | ELANE | ENPP3 | NNMT | SLC34A2 | STC1 | 1.882 | 1.833 |
| CTSB | ELANE | GRN | LCN2 | NNMT | STC1 | 1.882 | 1.833 |
| CTSB | ELANE | GRN | MMP26 | NNMT | SDCBP2 | 1.882 | 1.833 |
| CTSB | ELANE | GRN | MSLN | NNMT | STC1 | 1.882 | 1.833 |
| CTSB | ELANE | GRN | MVP | NNMT | SLC26A2 | 1.966 | 1.833 |
| CTSB | ELANE | GRN | NNMT | PGR | SLC26A2 | 1.882 | 1.833 |
| CTSB | ELANE | GRN | NNMT | PGR | SLC34A2 | 1.882 | 1.833 |
| CTSB | ELANE | GRN | NNMT | PGR | STC1 | 1.966 | 1.833 |
| CTSB | ELANE | LCN2 | MMP26 | NNMT | PGR | 1.882 | 1.833 |
| CTSB | ELANE | LCN2 | NNMT | PGR | SLC26A2 | 1.882 | 1.833 |
| CTSB | ELANE | MMP26 | NNMT | PGR | STC1 | 1.882 | 1.833 |
| CTSB | ELANE | MMP26 | NNMT | PGR | TCN1 | 1.882 | 1.833 |
| CTSB | ELANE | MMP26 | NNMT | SDCBP2 | SLC34A2 | 1.882 | 1.833 |
| CTSB | ELANE | MMP26 | NNMT | SLC34A2 | STC1 | 1.882 | 1.833 |
| CTSB | ELANE | MSLN | NNMT | PGR | SLC26A2 | 1.882 | 1.833 |
| CTSB | ELANE | MSLN | NNMT | SLC26A2 | SLC34A2 | 1.931 | 1.833 |
| CTSB | ELANE | MSLN | NNMT | SLC26A2 | TCN1 | 1.848 | 1.833 |
| CTSB | ELANE | MVP | NNMT | SLC26A2 | SLC34A2 | 1.966 | 1.833 |
| CTSB | ELANE | NNMT | PGR | SLC26A2 | TCN1 | 1.966 | 1.833 |
| CTSB | ELANE | NNMT | PGR | SLC34A2 | TCN1 | 1.882 | 1.833 |
| CTSB | ELANE | NNMT | RNASET2 | SLC26A2 | TCN1 | 1.882 | 1.833 |
| CTSB | ELANE | NNMT | SLC26A2 | STC1 | TCN1 | 1.882 | 1.833 |
| CTSB | ENPP3 | LCN2 | MMP26 | NNMT | STC1 | 1.882 | 1.833 |
| CTSB | ENPP3 | LCN2 | NNMT | PGR | STC1 | 1.882 | 1.833 |
| CTSB | ENPP3 | LCN2 | NNMT | SLC26A2 | TCN1 | 1.848 | 1.833 |
| CTSB | ENPP3 | LCN2 | NNMT | STC1 | TCN1 | 1.848 | 1.833 |
| CTSB | ENPP3 | NNMT | PGR | RNASET2 | STC1 | 1.882 | 1.833 |
| CTSB | ENPP3 | NNMT | PGR | STC1 | TCN1 | 1.882 | 1.833 |
| CTSB | GRN | LCN2 | MVP | NNMT | SLC26A2 | 1.848 | 1.833 |
| CTSB | LCN2 | MMP26 | NNMT | PGR | STC1 | 1.882 | 1.833 |
| CTSB | LCN2 | MMP26 | NNMT | RNASET2 | STC1 | 1.882 | 1.833 |
| CTSB | LCN2 | MSLN | NNMT | PGR | STC1 | 1.848 | 1.833 |
| CTSB | LCN2 | MSLN | NNMT | RNASET2 | STC1 | 1.848 | 1.833 |
| CTSB | LCN2 | NNMT | PGR | RNASET2 | STC1 | 1.882 | 1.833 |
| CTSB | LCN2 | NNMT | PGR | SLC26A2 | TCN1 | 1.848 | 1.833 |
| CTSB | LCN2 | NNMT | PGR | STC1 | TCN1 | 1.882 | 1.833 |
| ELANE | ENPP3 | GRN | NNMT | PGR | STC1 | 1.882 | 1.833 |
| ELANE | ENPP3 | NNMT | PGR | SDCBP2 | STC1 | 1.848 | 1.833 |
| ELANE | ENPP3 | NNMT | PGR | STC1 | TCN1 | 1.848 | 1.833 |
| ELANE | GRN | NNMT | PGR | SLC26A2 | TCN1 | 1.848 | 1.833 |
| ELANE | LCN2 | MSLN | NNMT | PGR | SLC26A2 | 1.882 | 1.833 |
| ELANE | MMP26 | NNMT | PGR | SDCBP2 | TCN1 | 1.848 | 1.833 |
| ELANE | MMP26 | NNMT | PGR | STC1 | TCN1 | 1.848 | 1.833 |
| ENPP3 | GRN | LCN2 | NNMT | PGR | STC1 | 1.848 | 1.833 |
| ENPP3 | LCN2 | MMP26 | NNMT | PGR | STC1 | 1.848 | 1.833 |
| ENPP3 | LCN2 | MSLN | NNMT | PGR | STC1 | 1.848 | 1.833 |
| ENPP3 | LCN2 | NNMT | PGR | RNASET2 | STC1 | 1.848 | 1.833 |
| ENPP3 | LCN2 | NNMT | PGR | SLC34A2 | STC1 | 1.848 | 1.833 |
| GRN | LCN2 | MMP26 | NNMT | PGR | STC1 | 1.848 | 1.833 |
| GRN | LCN2 | NNMT | PGR | RNASET2 | STC1 | 1.848 | 1.833 |
| LCN2 | MMP26 | MSLN | NNMT | PGR | STC1 | 1.848 | 1.833 |
| LCN2 | MMP26 | NNMT | PGR | RNASET2 | TCN1 | 1.848 | 1.833 |

In an embodiment, measuring the respective amount comprises measuring, in the UF sample taken from the human female subject, a respective amount of six proteins as listed in any of the UF protein panels shown in Table 4.

In a particular embodiment, the method comprises measuring, in the UF sample taken from the human female subject, the respective amount of nicotinamide N-methyltransferase encoded by the gene NNMT and the respective amount of at least two proteins, preferably at least three proteins, selected from the group consisting of, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2.

In this particular embodiment, the amount of amount of nicotinamide N-methyltransferase encoded by the gene NNMT is measured in addition to at least two, such as at least three, other proteins selected from Table 7. Thus, the UF protein panel comprises nicotinamide N-methyltransferase encoded by the gene NNMT in this particular embodiment.

In an embodiment, the method comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR. The method also comprises comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR.

In this embodiment, the UF protein panel comprises nicotinamide N-methyltransferase (NNMT), neutrophil gelatinase-associated lipocalin (LCN2) and progesterone receptor (PGR). In an embodiment, the UF protein panel may comprise at least one additional protein selected from Table 7. For instance, the method could comprise measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR and an amount of sulfate transporter encoded by the gene SLC26A2 and/or of sodium-dependent phosphate transport protein 2B encoded by the gene SLC34A2, preferably sulfate transporter encoded by the gene SLC26A2. In such a case, the method also comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR and control amount of sulfate transporter encoded by the gene SLC26A2 and/or of sodium-dependent phosphate transport protein 2B encoded by the gene SLC34A2, preferably sulfate transporter encoded by the gene SLC26A2.

In the above illustrative embodiment, the UF protein panel comprises, preferably consists of, nicotinamide N-methyltransferase (NNMT), neutrophil gelatinase-associated lipocalin (LCN2), progesterone receptor (PGR) and sulfate transporter (SLC26A2), or nicotinamide N-methyltransferase (NNMT), neutrophil gelatinase-associated lipocalin (LCN2), progesterone receptor (PGR) and sodium-dependent phosphate transport protein 2B (SLC34A2); or nicotinamide N-methyltransferase (NNMT), neutrophil gelatinase-associated lipocalin (LCN2), progesterone receptor (PGR), sulfate transporter (SLC26A2) and sodium-dependent phosphate transport protein 2B (SLC34A2).

A currently preferred UF protein panel is nicotinamide N-methyltransferase (NNMT), neutrophil gelatinase-associated lipocalin (LCN2), progesterone receptor (PGR) and sulfate transporter (SLC26A2) having a combined sensitivity and specificity for MSE vs. MSE RIF of 1.882 and a combined sensitivity and specificity for ESE vs. MSE of 1.933 as shown in Table 2.

The respective amounts of the at least three proteins as measured in the UF sample are compared with respective control amounts of the at least three proteins. The control amounts of the at least three proteins could be amounts of the at least three proteins taken from a previous UF sample from the human female subject, such as when using the UF protein panel to differentiating between ESE phase or MSE phase, or between a receptive endometrium or a non-receptive endometrium. For instance, the control amounts of the at least three proteins could be measured in an UF sample taken from the human female subject when she is known to be in a non-receptive phase of the menstruation cycle, such as in an ESE phase, or when she is known to be in a receptive phase of the menstruation cycle, such as in the MSE phase. In another embodiment, the control amounts of the at least three proteins could be average or median amounts of the at least three proteins measured in UF samples taken from multiple fertile human female control subjects, i.e., multiple fertile control women. The UF samples are then preferably taken from the multiple control women when being a same or substantially same phase of the menstruation cycle.

In the embodiments of differentiating between RIF MSE phase and MSE phase, the control amounts of the at least three proteins could be amounts of the at least three proteins taken from multiple healthy control women, i.e., human female subjects not suffering from RIF.

The determination of the EM receptivity status of the human female subject is then performed based on the comparison, i.e., whether there is any significant change in the amounts of the measured at least three proteins in the UF sample as compared to the respective control amounts. Table 5 and 7 indicate the direction of change in the MSE phase versus the ESE phase for the 21 proteins (marked in bold in Table 5). As is shown in Table 5 and Table 7, the levels of all 21 proteins except progesterone receptor (PGR) significantly increased in the MSE phase as compared to the ESE phase and between MSE and RIF MSE phase.

TABLE 5

| Protein | mean FC (MSE vs ESE) | p value (paired) (MSE vs ESE) | mean FC (MSE vs RIF MSE) | p value (MSE vs RIF MSE) |
|---|---|---|---|---|
| SFRP4 | 0.08 | 1.62208E–05 | 2.49 | 0.00344123 |
| PALLD | 0.32 | 3.85588E–05 | 1.29 | 0.39386004 |
| MVP | 7.41 | 0.000120583 | 2.19 | 0.04747161 |
| SDCBP2 | 179.84 | 0.000183792 | 5.83 | 0.0128268 |
| PGR | 0.19 | 0.000215573 | 0.29 | 0.00033522 |
| NNMT | 28.20 | 0.00026547 | 2.29 | 0.00816249 |
| PARP4 | 11.07 | 0.000291973 | 1.57 | 0.47188595 |
| SDC2 | 0.28 | 0.001182984 | 1.35 | 0.94145525 |
| CDH11 | 0.27 | 0.001396486 | 1.17 | 0.52251418 |
| PGRMC1 | 0.48 | 0.00145134 | 3.29 | 0.01297651 |
| SFRP1 | 0.31 | 0.001574565 | 1.42 | 0.05636413 |
| CD55 | 70.07 | 0.001587659 | 12.02 | 1.4447E–06 |
| HGD | 29.53 | 0.0016363 | 1.29 | 0.57577987 |
| LCN2 | 20.23 | 0.001875422 | 18.61 | 1.6789E–09 |
| SLC26A2 | 77.46 | 0.002041398 | 18.99 | 0.00041007 |
| ENPP3 | 51.25 | 0.002148628 | 19.14 | 0.00045102 |
| CTSB | 8.06 | 0.002782799 | 9.88 | 3.0776E–08 |
| MAP3K5 | 20.11 | 0.003447004 | 1.43 | 0.98936329 |
| GRN | 295.60 | 0.003453997 | 8.65 | 0.0093464 |
| TCN1 | 78.91 | 0.003955968 | 6.35 | 2.6827E–05 |
| DPP4 | 57.22 | 0.004031865 | 6.75 | 3.1474E–05 |
| POSTN | 0.27 | 0.004181335 | 1.76 | 0.03029095 |
| ELANE | 82.94 | 0.00488655 | 38.24 | 2.3558E–05 |
| MPO | 381.71 | 0.0061079 | 39.55 | 6.8026E–06 |
| BCAT1 | 8.97 | 0.006601044 | 3.36 | 0.48090183 |
| STC1 | 1255.13 | 0.006720452 | 9.04 | 0.00185201 |
| SLC34A2 | 77.96 | 0.008908338 | 10.73 | 0.00197729 |
| PAEP | 144285.10 | 0.00981439 | 9.31 | 0.15536068 |
| CRISP3 | 17.40 | 0.0105502 | 21.85 | 0.00027071 |
| MMP26 | 204.40 | 0.010614719 | 9.23 | 0.27396763 |
| ISYNA1 | 0.57 | 0.012162747 | 1.28 | 0.63155311 |
| COL7A1 | 0.42 | 0.014500894 | 1.88 | 0.19124517 |
| AOC1 | 230.36 | 0.019300334 | 7.60 | 0.01391812 |
| COMP | 157.87 | 0.02254324 | 8.33 | 0.06163359 |
| RNASET2 | 9.53 | 0.023102363 | 5.86 | 3.9371E–05 |
| ALDH1A3 | 0.74 | 0.03296585 | 0.82 | 0.10233452 |
| MSLN | 39.98 | 0.039282994 | 28.96 | 5.0072E–05 |
| PAMR1 | 0.40 | 0.039808208 | 4.05 | 0.03083356 |
| IGFBP7 | 92.12 | 0.052029032 | 8.89 | 0.02122177 |
| GBP2 | 2.28 | 0.056824019 | 1.43 | 0.786054 |
| PIGR | 24.16 | 0.108901879 | 8.73 | 1.562E–08 |
| CD36 | 283.35 | 0.143432476 | 8.66 | 0.17000009 |
| ITGA6 | 1.36 | 0.208543187 | 8.57 | 0.00980583 |
| CAND2 | 2.92 | 0.317195435 | 1.28 | 0.62460788 |
| IL6ST | 19.84 | 0.321972842 | 11.95 | 0.00024214 |

A significant change as used herein is preferably determined by fold change (FC). FC is a measure describing how much an amount of a protein changes between two different measurements or situations, such as FC=MSE/ESE in the case of fold change MSE vs. ESE. A significant change as represented by FC is preferably a FC≥X (increase in amount of protein) or a FC≤1/X (decrease in the amount of protein). X is a positive number equal to or larger than 2, preferably equal to or larger than 3, more preferably equal to or larger than 4, such as equal to or larger than 5.

In an embodiment, the respective amounts of the at least one three proteins are measured using a respective antibody that specifically binds to the respective protein of the at least three proteins selected from the group.

The antibodies may be polyclonal antibodies, monoclonal antibodies or one them may be a polyclonal antibody with the other as a monoclonal antibody. One or more of the antibodies may be an antibody fragment having specificity for the relevant protein. In such a case, the fragment can be selected from a group consisting of a single chain antibody, a Fv fragment, a scFv fragment, a Fab fragment, a F(ab')2 fragment, a Fab' fragment, a Fd fragment, a single-domain antibody (sdAb), a scFv-Fc fragment, a di-scFv fragment and a CDR region.

The specificity of an antibody can be determined based on affinity and/or avidity. The affinity, represented by the equilibrium constant for the dissociation of an antigen with the antibody ($K_D$), is a measure for the binding strength between an antigenic determinant and an antigen-binding site on the antibody. The lesser the value of $K_D$, the stronger the binding strength between the antigenic determinant and the antibody. Alternatively, the affinity can also be expressed as the affinity constant ($K_A$), which is $1/K_D$. As will be clear to the skilled person, affinity can be determined in a manner known per se, depending on the specific antigen of interest.

Avidity is the measure of the strength of binding between an antibody and the pertinent antigen. Avidity is related to both the affinity between an antigenic determinant and its antigen binding site on the antibody and the number of pertinent binding sites present on the monoclonal antibody.

Typically, antibodies will bind to their antigen with a dissociation constant ($K_D$) of $10^{-5}$ to $10^{-12}$ moles/liter (M) or less, and preferably $10^{-7}$ to $10^{-12}$ M or less and more preferably $10^{-8}$ to $10^{-12}$ M, i.e. with an association constant ($K_A$) of $10^5$ to $10^{12}$ M$^{-1}$ or more, and preferably $10^7$ to $10^{12}$ M$^{-1}$ or more and more preferably $10^8$ to $10^{12}$ M$^{-1}$.

Generally, any $K_D$ value greater than $10^{-4}$ M (or any $K_A$ value lower than $10^4$ M$^{-1}$) is generally considered to indicate non-specific binding.

In a particular embodiment, the respective amounts of the at least three proteins are measured in the UF sample using respective Enzyme-Linked Immunosorbent Assay (ELISA) kits, such as sandwich ELISA kits.

A sandwich ELISA can be used to detect a protein in a UF sample by preparing a surface of a support, such as a solid support, to which a first antibody is bound as so-called capture antibody. In a preferred embodiment, a known quantity of the first antibody is bound to the surface of the support. Any nonspecific binding sites on the surface are optionally but preferably blocked. The UF sample is then applied to the surface so that any protein present therein and for which the first antibody has specificity will be captured by the immobilized first antibodies. Unbound material is preferably removed by one or multiple washing steps. A second antibody, typically denoted detection antibody, is then added and is allowed to bind to the protein captured by the first antibody.

The amount of bound second antibody is then determined by direct or indirect detection methods. For instance, a label or enzyme can be attached directly to the second antibody or indirectly via a link, such as a biotin-streptavidin or a biotin-avidin link. It is, alternatively, possible to use a secondary antibody that is labeled or connected to an enzyme and binds specifically to the second antibody.

Hence, in an embodiment the second antibody has a covalently attached biotin. Alternatively, the second antibody has a covalently attached streptavidin or avidin.

The kit preferably also comprises a horseradish peroxidase (HRP) labeled streptavidin or a HRP labeled avidin. Alternatively, the kit also comprises a HRP labeled biotin. The kit also comprises a HRP substrate, such as a 3,3',5,5'-tetramethylbenzidine (TMB) substrate, a 3,3'-diaminobenzidine (DAB) substrate or a 2,2'-azino-bis(3-ethylbenzothiazoline-6-sulphonic acid (ABTS) substrate. In such a case, the level of protein in the UF sample can be determined by spectrophotometric methods that detect the conversion of the chromogenic substrate by HRP into a colored product that is detectable.

The above mentioned first and second antibodies having specificity for a protein in Table 7 could be the same antibodies, i.e., binds specifically to the same epitope on the protein. In another embodiment, the first and second antibodies have specificity to different epitopes on the protein and are thereby different antibodies.

In an embodiment, the kit also comprises a microtiter plate (MCP) as the support to which the first antibody is immobilized or is intended to be immobilized.

The kit does not necessarily have to be an ELISA kit. In another embodiment, the kit uses affinity chromatography where the first antibody is bound to the stationary phase, such as to a gel matrix or beads in a column. For instance, the gel matrix or beads could be made of agarose, such as SEPHAROSE®. In such a case, the protein present in a UF sample will be entrapped in the column through binding to the immobilized first antibodies. Following washing, the bound protein can be eluted and detected using the first or second antibody. For instance, the amount of eluted protein can be determined using Western blotting and with the first or second antibody for protein detection using direct or indirect detection methods.

The support could alternatively be magnetic beads, such as DYNABEADS® magnetic beads.

In an embodiment, the UF sample taken from the human female subject is used directly in the antibody-based measurement of the at least proteins. In another embodiment, the UF sample may be subject to one or more centrifugations prior to protein measurements. In such a case, the supernatants from such centrifugation(s) containing proteins is (are) used in the protein measurements, whereas any pellet(s) containing cell debris and other larger material is (are) discarded.

In another embodiment, the respective amounts of the at least three proteins are measured by separating proteins from the UF sample taken from the human female subject on a two-dimensional gel electrophoresis (2-DE) gel. The at least three proteins selected from the group are identified on the 2-DE gel. The method also comprises measuring a respective amount of the identified at least three proteins selected from the group on the 2-DE gel.

In this embodiment, the 2-DE separates the proteins based on isoelectric point and mass. Thus, a first separation step is isolectric focusing where the proteins are separated based on their isoelectric point. A second separation step separates the proteins based on their molecular weight or mass using SDS-PAGE.

The proteins on the 2-DE gel can be marked to enable identification of the relevant proteins and the subsequent measurement of the amount of the proteins. Various protein marking protocols and methods can be used, such as silver staining. In such a case, the silver staining is preferably performed using a mass spectrometry compatible staining protocol. The stained proteins can then be scanned and the respective amount of the at least three proteins can be determined from the images of the stained 2-DE gel.

Other techniques and methods for measuring the respective amounts of the at least three proteins in the UF sample are possible and within the scope of the embodiments including, for instance, mass spectrometry, a multiplex Luminex® microsphere test, and multiple reaction monitoring (MRM).

In an embodiment, the method also comprises determining a day for embryo transfer in an IVF cycle for the human female subject based on the determined EM receptivity status, i.e., based on the comparison. In a particular embodiment, the method also comprises implanting an embryo into a uterus of the human female subject at the determined day for embryo transfer.

Hence, the embodiments can be used to determine the most appropriate day for embryo transfer in an IVF cycle and thereby schedule embryo implantation to occur at that day when the endometrium is determined using the UF protein panel of the embodiments to be most receptive for embryo implantation. This means that the embodiments will increase the chances for successful embryo transfer, and in particular for RIF patients.

The embodiments also relates to a kit for determining endometrial (EM) receptivity status of a human female subject. The kit comprises, in an embodiment, antibodies for measuring, in a uterine fluid (UF) sample taken from the human female subject, a respective amount of at least three proteins selected from the group consisting of nicotinamide N-methyltransferase encoded by the gene NNMT, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2. The kit also comprises instructions for determining EM receptivity status of the human female subject based on a comparison of the respective amount with a respective control amount of the at least three proteins.

In an embodiment, the kit comprises information of the control amount of the at least three proteins.

In an embodiment, the kit comprises multiple ELISA kits, preferably one such ELISA kit per protein of the at least three proteins.

EXAMPLES

Current endometrial (EM) receptivity assays are based on analyzing transcriptomic patterns of EM biopsies at the time of window of implantation (WOI). Biopsy is invasive and cannot be performed in the same cycle with in vitro fertilization (IVF) and embryo transfer. In clear contrast, uterine fluid (UF) aspirate analysis is minimally invasive and can be used immediately before IVF embryo transfer. The difficult patient group with recurrent implantation failure (RIF) is expected to benefit the most from the development of reliable molecular tools to analyze UF biomarkers before IVF embryo transfer. Moreover, the UF proteome studies would bring more clarity to, so far unclear, RIF pathogenesis, where both displaced and disrupted WOI molecular changes have been speculated to cause infertility.

Figure 9:
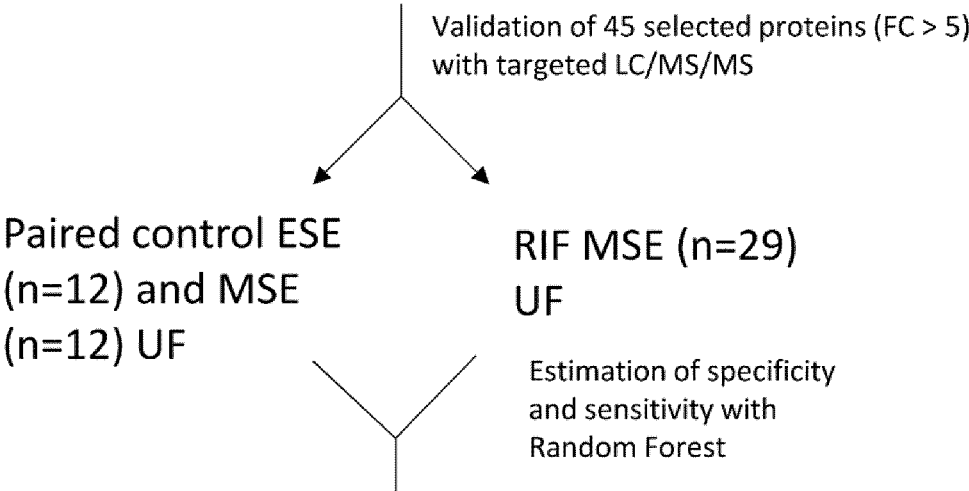
FIG. 9. Overview of the experimental design for determining proteomic receptivity biomarkers from uterine fluid. Abbreviations: ESE, early secretory phase; MSE, mid-secretory phase; UF, uterine fluid; FDR, false discovery rate; FC, fold change; LC/MS/MS, liquid chromatography tandem-mass spectrometry; RIF, recurrent implantation failure.

The present examples used paired UF sample analysis with mass spectrometry (MS) based proteomics with a discovery and a validation phase to determine whether the UF proteome can be used for EM receptivity monitoring and whether uterine secretome would help to highlight the causes behind RIF (FIG. 9). The analysis was performed on early secretory (ESE) and mid-secretory phase (MSE)

samples from controls, and mid-secretory samples from women with RIF (RIF MSE).

3,158 proteins were detected from secretory phase UF of which 367 underwent significant (q<0.05) proteomic changes during the transition from ESE to MSE phase. 45 proteins were further selected for validation using targeted MS-proteomics in a standalone cohort. Of these, 38 were validated (p<0.05) for control samples and 19 displayed similar levels between control ESE and RIF MSE, indicating possible displacement of WOI. A panel of four proteins (PGR, NNMT, SLC26A2 and LCN2) was estimated as optimal for monitoring EM receptivity, demonstrating both a specificity and sensitivity of 91.7% for distinguishing MSE samples from ESE samples. The same panel distinguished control MSE samples from RIF MSE with a 91.7% specificity and 96.6% sensitivity.

Methods

Ethical Approval

The study was approved by the regional ethics committee at Stockholm, Sweden (approval no. 2016/794-31/4) and at Tartu, Estonia (approval no. 276/M-15). Informed written consent was obtained from all participants.

Study Participants and Uterine Fluid Sample Collection

Paired UF samples were collected from six fertile control women (mean age: 31.0 years, range: 29-33; mean body mass index (BMI): 23.5 kg/m², range: 20.4-31.1) with proven parity. In the discovery cohort, women with polycystic ovary syndrome (PCOS), premature ovarian insufficiency (POI) and/or uterine pathologies (uterine fibroids, adenomyosis and endometriosis) were excluded. Urinary luteinizing hormone (LH) test was used to determine the day of the LH surge (LH+0). The first of the paired samples was collected one to three days after the LH surge (LH+1/+3 or in early secretory endometrial phase, ESE), while the second collection was performed on days LH+7 to +9 (MSE) in the same natural menstrual cycle. UF was obtained by lavage after flushing the uterus with 0.5 ml of phosphate buffered saline (PBS) for 30 seconds and then aspirating the fluid. The procedure was carried out with an intrauterine insemination catheter (Cooper Surgical, Connecticut, USA) inserted through the cervical canal into the uterine cavity, while avoiding touching the uterine fundus. Samples were centrifuged at 2,000 rpm for 5 min at 4° C. on a benchtop centrifuge, after which the supernatant was transferred to a new tube and stored at −80° C. After collection of the UF at MSE, an EM biopsy for histological EM dating was obtained by Pipelle catheter (Laboratoire CCD, Paris, France).

For the validation study, 12 volunteers (n=12 paired samples) were recruited from different clinics. The validation control group consisted of women (mean age: 29.3 years, range: 22-36; mean BMI: 23.7 kg/m², range: 18.9-31.1) undergoing the first cycle of IVF treatment for male- or tubal-factor infertility. Women with history of PCOS, POI or uterine pathologies were excluded. The UF collection was performed as described above but EM biopsy was not performed.

The RIF MSE cohort (n=29) consisted of women (mean age: 35.7 years, range 26-42; mean BMI: 23.6 kg/m², range: 19.0-38.9) who had had at least three (n≥3) unsuccessful IVF cycles (median: 4, range: 3-10). All RIF women were diagnosed with male- or tubal-factor infertility. Women with PCOS, POI or with uterine pathologies were excluded. The women's age did not correlate with the number of failed IVF cycles (r=0.17). EM fluid lavage and EM biopsy were performed during MSE (LH+7 to +9) as described above.

Sample Preparation for Discovery Proteomics

All samples were processed in a randomized order with a blocking design (Oberg & Vitek 2009). UF samples were thawed on ice and prepared for XCell SureLock Mini (Invitrogen, California, U.S.) SDS-PAGE system according to manufacturer's instructions. NuPAGE (Invitrogen) 4-12% Bis-Tris gradient gels (Invitrogen) were used with the system. After gel staining with SimplyBlue SafeStain (Invitrogen), each lane was sliced into six fractions and subjected to the in-gel digestion protocol. Briefly, gel bands were destained in 1:1 acetonitrile (ACN):100 mM ammonium bicarbonate (ABC) with vortexing, reduced with 10 mM dithiothreitol (DTT) at 56° C. and alkylated with 50 mM iodoacetamide in the dark. The bands were digested overnight with 10 ng/μl of dimethylated porcine trypsin (Sigma Aldrich, Missouri, U.S.) in 100 mM ABC at 37° C. Peptides were extracted from the gel matrix using bath sonication, followed by 30 min vortexing in 2 volumes of 1:2 5% formic acid (FA):ACN. The organic phase was evaporated in a vacuum-centrifuge, after which the peptides were desalted on in-house made C18 (3M, Minnesota U.S.) solid phase extraction tips. Purified peptides were reconstituted in 0.5% TFA for nano-liquid chromatography tandem-mass spectrometry (LC/MS/MS).

Sample Preparation for Targeted Proteomics

All samples were processed in a randomized order. Proteins were precipitated with 10% (w/v) trichloroacetic acid overnight at 4° C., pelleted at 17,000×g 4° C. and washed twice with cold 90% (v/v) acetone. Protein concentration was determined with the Micro-BCA assay (Thermo Fisher Scientific, Massachusetts, U.S.). 15 μg of precipitated proteins were then solubilized in 7 M urea, 2 M thiourea, 100 mM ABC buffer, reduced with 5 mM DTT for 30 min at room temperature (RT, 20-25° C.) and alkylated with 20 mM chloroacetamide at RT in the dark. Pre-digestion with 1:50 (enzyme to protein ratio) Lys-C (Fujifilm Wako Pure Chemical, Osaka, Japan) was carried out for 4 h at RT. Next, the solution was diluted five times with 100 mM ABC and a further digestion with 1:50 dimethylated trypsin (Sigma Aldrich) was carried out overnight at RT. Samples were then acidified with TFA to 1.0% and desalted on in-house made C18 SPE tips. Purified peptides were reconstituted in 0.5% TFA for nano-LC/MS/MS.

Isolation of Endometrial Glands

To characterize enrichment of different categories of proteins in UF relative to glandular tissue, EM glands were purified from a freshly obtained EM biopsy. The separation of glandular cells from the remaining tissue and its subsequent lysis were carried out as described in (Kasvandik et al. 2016), except that sedimented epithelial glands were used instead of the supernatant-retained cellular material. Protein precipitation from the lysate and further sample preparation was carried out by the in-solution digestion protocol as described above for the validation set samples.

Discovery LC/MS/MS Analysis

Peptides from each gel fraction were injected to an Ultimate 3000 RSLCnano system (Dionex, California, U.S.) using a 0.3×5 mm trap-column (5 μm C18 particles, Dionex) and an in-house packed (3 μm C18 particles, Dr Maisch, Ammerbuch, Germany) analytical 50 cm×75 μm emitter-column (New Objective, Massachusetts, U.S.). Peptides were eluted at 200 nl/min with an A to B 8-40% 2 h gradient (buffer A: 0.1% FA, buffer B: 80% ACN+0.1% FA) to a quadrupole-orbitrap Q Exactive Plus (Thermo Fisher Scientific) MS/MS via a nano-electrospray source (positive mode, spray voltage of 2.5 kV). The MS was operated with a top-5 data-dependent acquisition strategy. Briefly, one 350-1,400 m/z MS scan at a resolution setting of R=70,000 at 200 m/z was followed by higher-energy collisional dissociation fragmentation (normalized collision energy of 26) of the 5 most intense ions (z: +2 to +6) at R=17,500. MS and MS/MS ion target values were 3,000,000 and 50,000 with 50 and 100 ms injection times, respectively. Dynamic exclusion was limited to 60 s.

Targeted LC/MS/MS Analysis

Desalted peptides were injected to an Ultimate 3000 RSLCnano system (Dionex) using a 0.3×5 mm trap-column (5 μm C18 particles, Dionex) and an in-house packed (3 μm C18, Dr Maisch) analytical 50 cm×75 μm emitter-column (New Objective). Peptides were eluted at 250 nl/min with an A to B 10-45% 90 min gradient (buffer A: 0.1% FA, buffer B: 80% ACN+0.1% FA) to a Q Exactive Plus (Thermo Fisher Scientific) MS/MS using a nano-electrospray source (positive mode, spray voltage of 2.6 kV). The MS was operated in a scheduled parallel reaction monitoring (PRM) mode by isolating and fragmenting only selected peptides from the validation set's proteins (Table 6) within ±3 minute windows of their retention times. Retention time scheduling was calibrated using the indexed retention time (iRT) method (Escher et al. 2012). MS/MS isolation window was 1.0 m/z with an ion target value and fill time of 200,000 ions and 160 ms, respectively. Normalized collision energy was set at 26.

TABLE 6

| Peptides used in the validation experiment for targeted MS | | | | | |
|---|---|---|---|---|---|
| Targeted m/z value | Charge state | iRT index | Peptide | Protein | SEQ ID NO: |
| 685.3899 | +2 | 70.89 | EEIFGPVQPILK | ALDH1A3 | 1 |
| 555.2955 | +2 | 16.87 | IAFTGSTEVGK | ALDH1A3 | 2 |
| 584.7853 | +2 | 27.95 | FYGSPEELAR | AOC1 | 3 |
| 592.3685 | +2 | 80.58 | DLIVTPATILK | BCAT1 | 4 |
| 390.2185 | +2 | -0.74 | EVVGTFK | BCAT1 | 5 |
| 536.2933 | +2 | -2.03 | NGEVQNLAVK | CAND2 | 6 |
| 352.7081 | +2 | 0.47 | GIPVYR | CD36 | 7 |
| 495.2761 | +2 | 13.36 | LTCLQNLK | CD55 | 8 |
| 515.2427 | +2 | -11.63 | SCPNPGEIR | CD55 | 9 |
| 828.4442 | +3 | 107.43 | LVYSILEGQPYFSVEAQTGIIR | CDH11 | 10 |
| 542.7853 | +2 | -5.36 | VLDVNDNAPK | CDH11 | 11 |
| 715.8779 | +2 | 38.25 | DLVLSEPSSQSLR | COL7A1 | 12 |
| 516.2595 | +2 | -20.57 | SSTGPGEQLR | COMP | 13 |
| 556.2405 | +2 | -8.33 | WANQCNYR | CRISP3 | 14 |
| 438.7323 | +2 | 9.46 | LPASFDAR | CTSB | 15 |
| 1003.4989 | +2 | 117.50 | NGPVEGAFSVYSDFLLYK | CTSB | 16 |
| 749.3905 | +2 | 68.54 | LAYVWNNDIYVK | DPP4 | 17 |
| 789.3939 | +2 | 55.18 | LGTFEVEDQIEAAR | DPP4 | 18 |
| 513.3087 | +2 | 21.39 | IGGIGTVPVGR | EEF1A1 | 19 |
| 435.7740 | +2 | 8.15 | QLIVGVNK | EEF1A1 | 20 |
| 355.8770 | +3 | -5.16 | VVLGAHNLSR | ELANE | 21 |
| 537.6316 | +3 | 75.41 | VHLFVDQQWLAVR | ENPP3 | 22 |
| 443.7189 | +2 | 6.47 | EYVSGFGK | ENPP3 | 23 |
| 702.3404 | +2 | -11.56 | AIAHYEQQMGQK | GBP2 | 24 |
| 694.8803 | +2 | 44.62 | EVVSAQPATFLAR | GRN | 25 |
| 501.7769 | +2 | 16.05 | GSEIVAGLEK | GRN | 26 |
| 510.5830 | +3 | 6.97 | VGAHAGEYGAEALER | HBA1 | 27 |
| 626.8610 | +2 | 57.54 | FLASVSTVLTSK | HBA1 | 28 |
| 621.8037 | +2 | 75.47 | FSIDVFEETR | HGD | 29 |

TABLE 6-continued

Peptides used in the validation experiment for targeted MS

| Targeted m/z value | Charge state | iRT index | Peptide | Protein | SEQ ID NO: |
|---|---|---|---|---|---|
| 588.3246 | +2 | 11.92 | QVPGGYTVINK | HGD | 30 |
| 759.3636 | +2 | 3.91 | AGAAAGGPGVSGVCVCK | IGFBP7 | 31 |
| 517.9558 | +3 | 66.19 | HEVTGWVLVSPLSK | IGFBP7 | 32 |
| 611.8375 | +2 | 51.28 | ILDYEVTLTR | IL6ST | 33 |
| 530.2953 | +2 | 38.83 | LTWINPSIK | IL6ST | 34 |
| 492.2453 | +2 | 26.14 | VFVGGDDFK | ISYNA1 | 35 |
| 498.2817 | +2 | 43.00 | FSYLPIQK | ITGA6 | 36 |
| 410.2266 | +2 | -4.88 | ELTSELK | LCN2 | 37 |
| 628.3377 | +2 | 67.09 | SYPGLTSYLVR | LCN2 | 38 |
| 690.8595 | +2 | 34.53 | LSALSAGSNEYLR | MAP3K5 | 39 |
| 494.2665 | +2 | -16.54 | IQHLYGEK | MMP26 | 40 |
| 647.3253 | +2 | 38.31 | TFQLSADDIQR | MMP26 | 41 |
| 576.8117 | +2 | 66.07 | IANVFTNAFR | MPO | 42 |
| 451.7382 | +2 | -26.79 | SPTLGASNR | MPO | 43 |
| 738.3907 | +2 | 54.67 | IQSFLGGAPTEDLK | MSLN | 44 |
| 354.8817 | +3 | 16.11 | LLGPHVEGLK | MSLN | 45 |
| 743.8490 | +2 | 11.16 | ALQPLEEGEDEEK | MVP | 46 |
| 565.8062 | +2 | 2.44 | IEGEGSVLQAK | MVP | 47 |
| 417.2035 | +3 | 27.16 | DTYLSHFNPR | NNMT | 48 |
| 438.7505 | +2 | 30.45 | FSSLPLGR | NNMT | 49 |
| 506.7747 | +2 | -17.61 | HSAESQILK | NNMT | 50 |
| 600.8424 | +2 | 84.31 | HLWYLLDLK | PAEP | 51 |
| 421.7345 | +2 | 12.59 | QDLELPK | PAEP | 52 |
| 649.8539 | +2 | 75.80 | GAPPLQVQWFR | PALLD | 53 |
| 647.3379 | +2 | 38.61 | YAALSDQGLDIK | PALLD | 54 |
| 465.2820 | +2 | 59.49 | PGFVIQLR | PAMR1 | 55 |
| 674.8226 | +2 | 40.32 | LELGNDWDSATK | PARP4 | 56 |
| 587.0123 | +3 | 66.94 | QLLGLQPISTVSPLHR | PARP4 | 57 |
| 549.7899 | +2 | 16.01 | APGASGCLLPR | PGR | 58 |
| 727.3770 | +2 | 25.92 | VALVEQDAPMAPGR | PGR | 59 |
| 782.4953 | +2 | 122.13 | VLLLLNTIPLEGLR | PGR | 60 |
| 758.8646 | +2 | 67.56 | FYGPEGPYGVFAGR | PGRMC1 | 61 |
| 512.7602 | +2 | 40.34 | GLATFCLDK | PGRMC1 | 62 |
| 470.7767 | +2 | 7.23 | ILLNPQDK | PIGR | 63 |
| 461.7533 | +2 | 23.42 | VYTVDLGR | PIGR | 64 |
| 656.8716 | +2 | 47.27 | IIDGVPVEITEK | POSTN | 65 |
| 661.3277 | +2 | -7.91 | ISTGGGETEETLK | POSTN | 66 |
| 572.3346 | +2 | 73.89 | ELDLNSVLLK | RNASET2 | 67 |

TABLE 6-continued

Peptides used in the validation experiment for targeted MS

| Targeted m/z value | Charge state | iRT index | Peptide | Protein | SEQ ID NO: |
|---|---|---|---|---|---|
| 631.8244 | +2 | 93.79 | SWPFNLEEIK | RNASET2 | 68 |
| 471.7356 | +2 | -26.92 | VHLSDSER | SDC2 | 69 |
| 631.3304 | +2 | 56.65 | FGDQLLQIDGR | SDCBP2 | 70 |
| 564.3120 | +2 | -7.58 | VDQAIQAQVR | SDCBP2 | 71 |
| 391.8924 | +3 | 23.77 | SQYLLTAIHK | SFRP1 | 72 |
| 495.7449 | +2 | -24.84 | LCHNVGYK | SFRP1 | 73 |
| 971.4955 | +2 | 91.64 | GVCISPEAIVTDLPEDVK | SFRP4 | 74 |
| 704.3428 | +2 | 18.87 | SGCNEVTTVVDVK | SFRP4 | 75 |
| 614.3423 | +2 | 72.25 | FVAPLYYINK | SLC26A2 | 76 |
| 513.3213 | +2 | 29.41 | QTVNPILIK | SLC26A2 | 77 |
| 773.3808 | +2 | -3.85 | YLEGAAGQQPTAPDK | SLC34A2 | 78 |
| 572.3095 | +2 | -17.66 | VAAQNSAEVVR | STC1 | 79 |
| 594.3534 | +2 | 63.46 | GTSAVNVVLSLK | TCN1 | 80 |
| 465.7356 | +2 | -13.70 | NGENLEVR | TCN1 | 81 |

Mass Spectrometric Raw Data Processing and Analysis

For the discovery data, MS raw files were processed with the MaxQuant software package (1.4.0.8) (Cox & Mann 2008). Methionine oxidation, and protein N-terminal acety-lation were set as variable modifications, while cysteine carbamidomethylation was defined as a fixed modification. Search was performed against UniProt (www.uniprot.org) human reference proteome database (downloaded: 2015 October) using the tryptic digestion rule (cleavages after lysine and arginine without proline restriction). Only iden-tifications with at least 1 peptide ≥7 amino acids long (with up to 2 missed cleavages) were accepted and transfer of identifications between runs based on accurate mass and retention time was enabled. Label-free normalization with MaxQuant LFQ algorithm was also applied. Protein and LFQ ratio count, i.e., number of quantified peptides for reporting a protein intensity, was set to 1. Peptide-spectrum match and protein false discovery rate (FDR) was kept below 1% using a target-decoy approach. All other param-eters were default. After peptide/protein identification and quantification, results were transferred to MaxQuant's Per-seus module, log2-transformed and filtered for at least 50% valid values in each group. Missing values were imputed by down-shifting and compressing the measured intensity dis-tributions by 1.8 and to 0.3 standard deviation units, respec-tively, thereby simulating intensity measurements on the measurement threshold.

For the targeted validation data, MS raw files were analysed with the Skyline software (MacLean et al. 2010). Spectral library was created from the discovery data. Pep-tides with the highest intensity in the library were preferred for the targeted analysis. No restrictions on peptide amino acid composition were enforced, as this was found to exclude many high intensity peptides. Only y-ions (starting from ion 3, $y_3$) with charge states +1 and +2 were allowed. All extracted ion chromatogram (XIC) integrations were manually inspected for correct peak picking. Fragment XIC traces with strong interference and erroneously picked peaks (mass errors >±20 ppm, lack of fragment coelution) were removed. All results were then exported and further pro-cessed with an in-house written R script. Peptide level peak areas were summed onto protein level, normalized using EEF1A1 intensities and log2 transformed. Missing values were imputed using MaxQuant's Perseus module. Imputa-tion was not applied for proteins in paired samples where both ESE and MSE had missing values.

Statistical and Bioinformatics Analyses

For the discovery data paired samples t-test was used with Storey's q-value method for multiple testing correction (Storey et al. 2003). Proteins with a q-value <0.05 were considered significantly different between ESE and MSE. The validation data was analysed either with the paired (for paired ESE and MSE samples) or independent (for MSE and RIF MSE samples) t-test, proteins were considered validated if p<0.05. No further correction for multiple testing was applied, as in validation data only preselected proteins each with a potential effect were considered, Principal component analysis (PCA) was used to study the ability of targeted proteins to distinguish different groups of samples in the validation dataset and was conducted with the R packages FactoMineR and factoextra (Le et al. 2008).

Random Forest approach was used to estimate the clas-sification accuracy, i.e., sensitivity and specificity, of protein sets consisting of 3 or 4 proteins out of the 21 proteins implicated in RIF WOI displacement and described in the results section. For Random Forest analysis the paired ESE and MSE samples were considered as independent samples both representing the random samples of studied phases, because in clinical practice requirement of paired samples is inconvenient and the decision about receptivity status must be made based on a single MSE sample, i.e., collected based on a post-LH-surge day. In that case the sensitivity and specificity estimates from Random Forest analyses are similar to the cross-validation estimates and restrain the over estimation of classification accuracy. The Random Forest analysis was conducted with the R package randomForest (Breiman 2001).

Term enrichment analyses were conducted with the Fun-Rich software package using UniProt 'Cellular localization' and Gene Ontology 'Biological process' terms (Pathan et al. 2015). Gene enrichment significance was calculated with the Fisher's exact test against the expressed human genome and corrected for multiple testing with the Benjamini-Hochberg's FDR method (Benjamini and Hochberg 1995).

Results

Comprehensive Protein Profiling of Uterine Fluid with Discovery Proteomics

For discovering potential receptivity-associated UF proteins, label-free discovery shotgun proteomics was first performed with paired samples collected at ESE and MSE from the same menstrual cycle from six fertile control women with at least one previous successful pregnancy.

The level of albumin in UF was high (FIG. 1), which leads to decreased depth of detection of co-eluting lower abundant peptide. To minimize this suppressive effect, gel fractionation and extended nano-LC/MS/MS measuring times were used. This approach enabled identification and quantification of 36,171 peptides belonging to 3,158 different proteins across samples of which 2,196 proteins met the set data completeness criteria for further statistical comparison, i.e., ≥50% valid values in either ESE or MSE group.

Figure 2A:
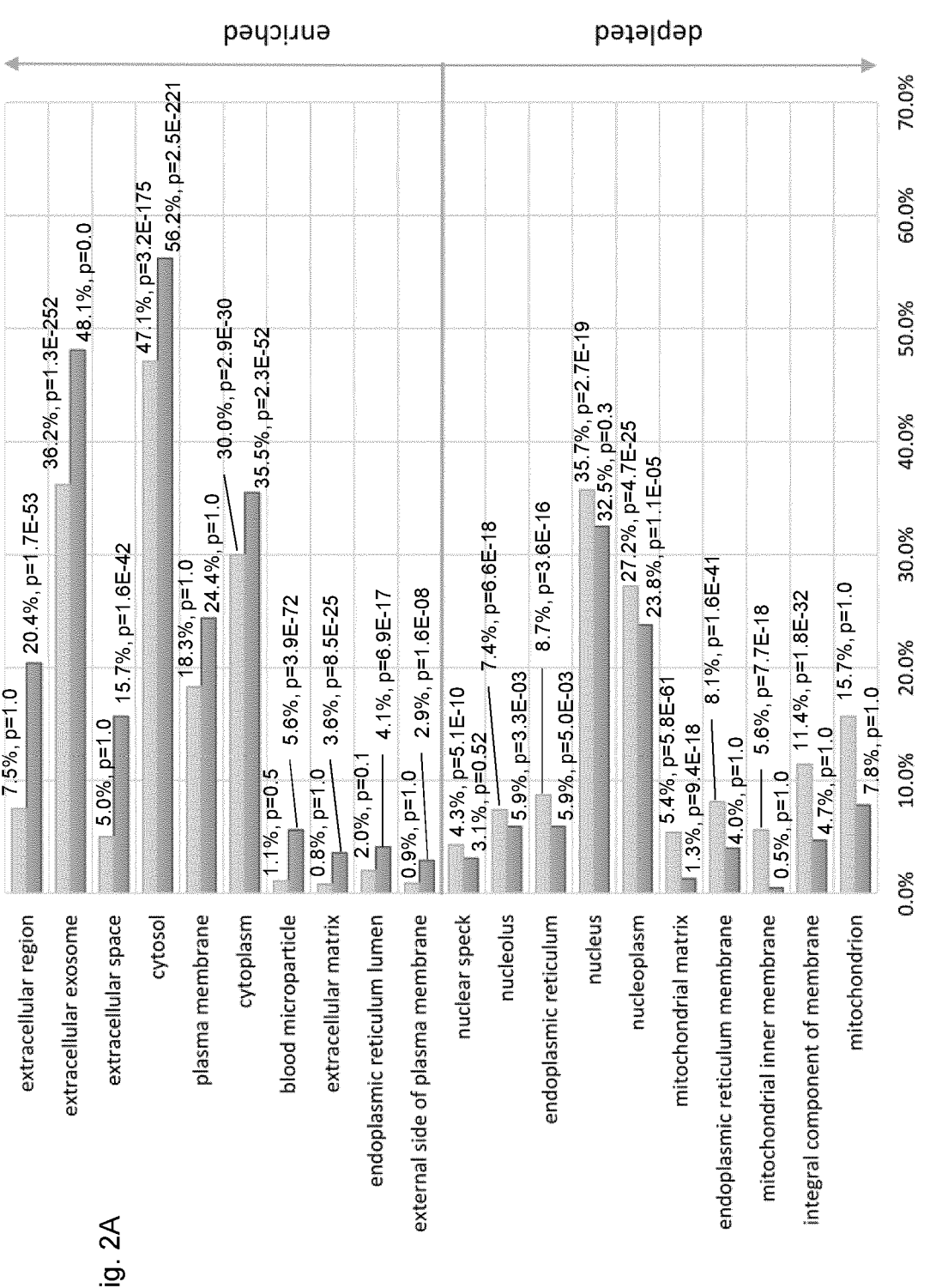
FIG. 2. Characterization of uterine fluid proteome composition. (A) Top ten UniProt 'cellular localization' terms showing the greatest magnitude of increase and decrease in the uterine fluid (lower bars) compared to endometrial glandular tissue (top bars). (B) Top ten Gene Ontology 'biological process' terms among MSE upregulated proteins. (C) Top ten Gene Ontology 'biological process' terms among MSE downregulated proteins. p-values of enrichment relative to the entire background human proteome have been indicated.

UniProt 'cellular localization' enrichment analysis indicated that relative to EM glandular tissue, UF contained more exosomal, extracellular and plasma membrane proteins, but also cytosolic and endoplasmic reticulum luminal proteins (FIG. 2A). It should be noted that many of these proteins have multiple reported cellular localizations, particularly proteins that are found in extracellular vesicles. Therefore, the exact origin of these intracellular proteins in UF cannot be ascertained at this stage. The fluid proteome is mainly depleted of mitochondrial, nuclear and endoplasmic reticulum membrane proteins compared to endometrial glandular tissue (FIG. 2A).

Figure 3A:
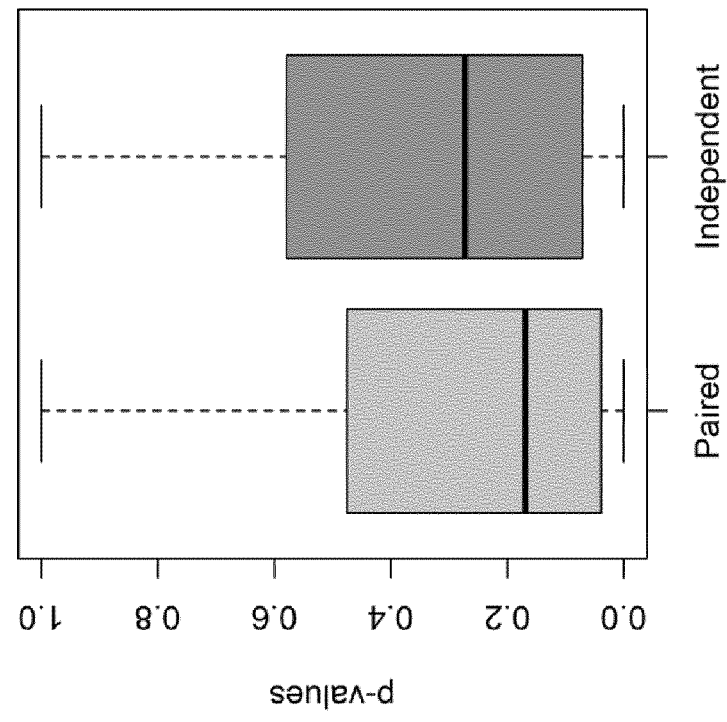
FIG. 3. (A) p-value distributions of uterine fluid ESE and MSE analysis with paired and independent groups test. The narrower and downward shifted distribution of paired p-values relative to independent ones indicates that a paired design is more adequate for discovery of receptivity associated differential expression. (B) Visualization of paired changes for a set of proteins from the discovery experiment.
Figure 3B:
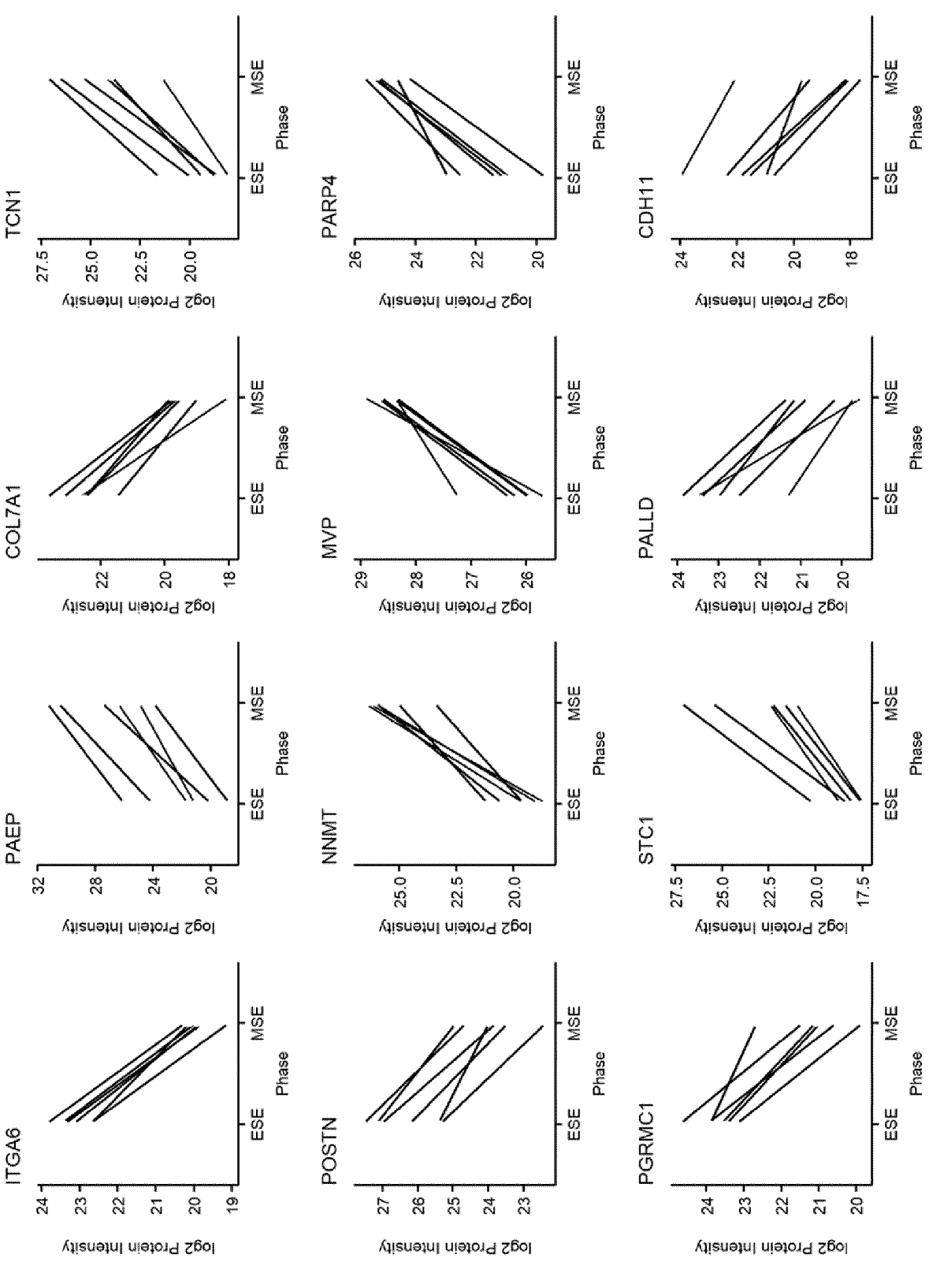
Figure 3B:
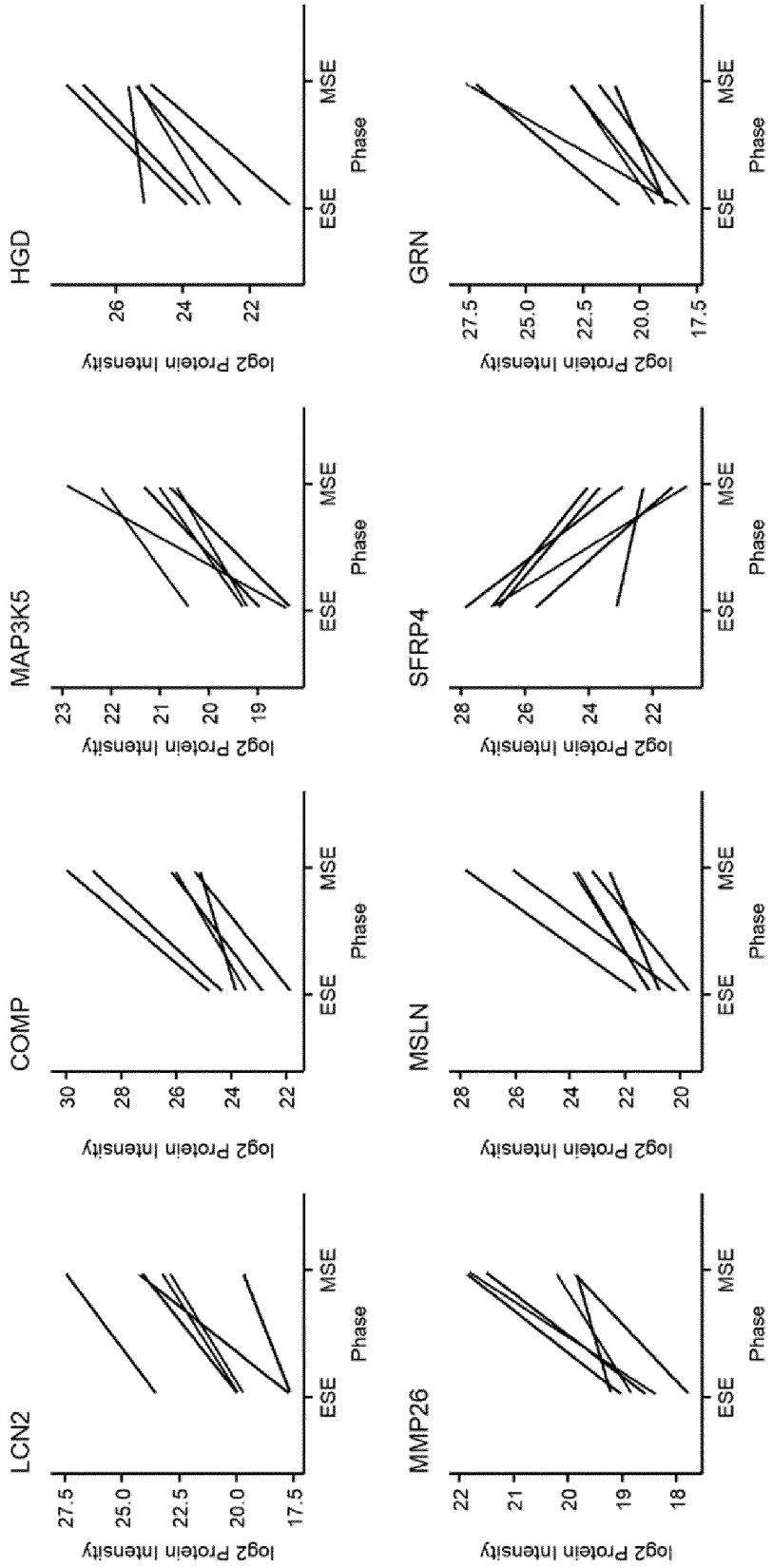

Uterine Fluid Proteome is Dynamically Altered During Transition from Early Secretory to Mid-Secretory Phase No studies have been published so far with the use of paired individual UF samples, so that one sample has been taken in ESE and the other in MSE phase of the same cycle. Paired samples enable more statistical power if the between-subjects variability is significant while within-subjects variability is lower. Indeed, smaller p-values were observed with paired analysis than with an independent one (FIG. 3A), which was also visually evident for many proteins with strong effect sizes in the discovery data (FIG. 3B). This demonstrated that for UF the between-subjects' variability was relevantly higher than that of within-subjects. Therefore, paired samples had advantages for maximizing discovery of receptivity-specific abundance differences in UF.

Figure 2B:
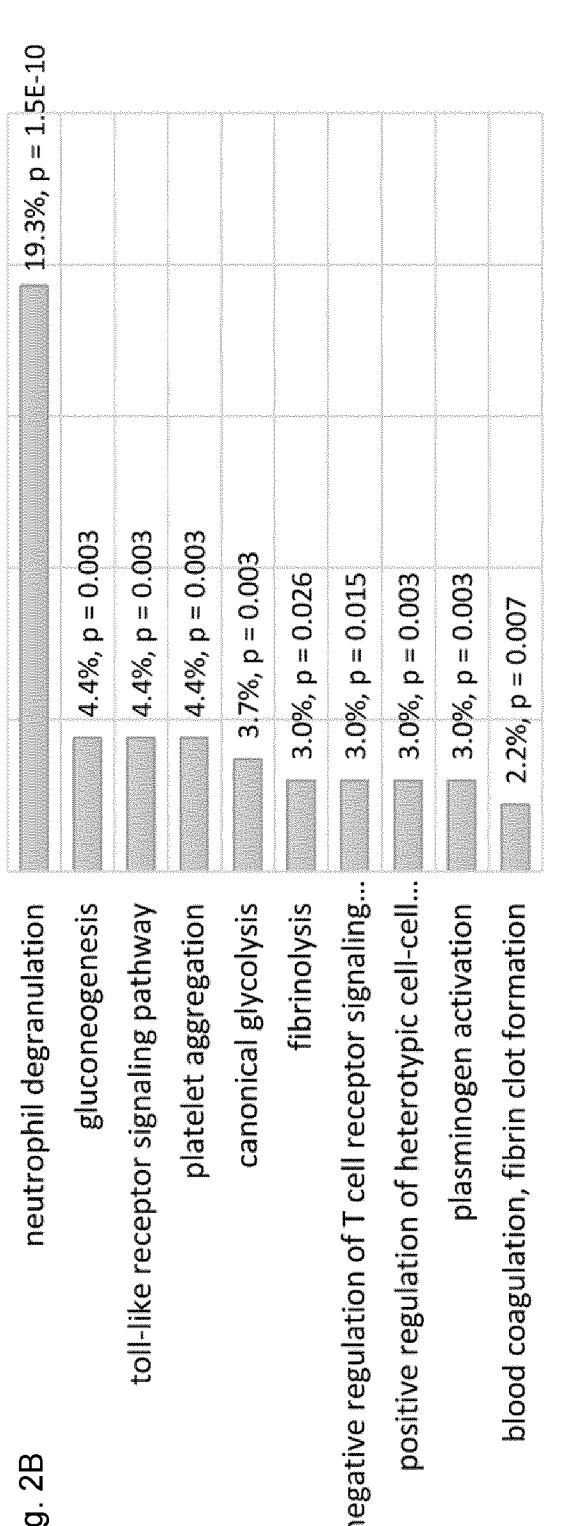
Figure 2C:
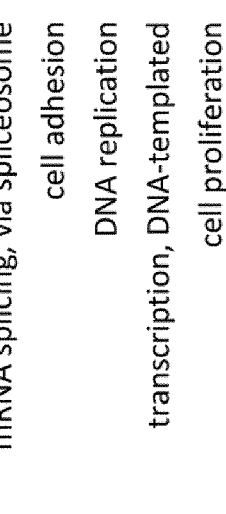
Figure 4:
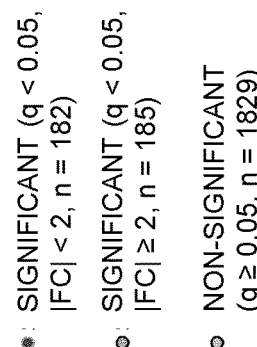
FIG. 4. Volcano plot summarizing the discovery proteomics experiment for MSE/ESE differences in fertile women. Data are presented as log2 of fold changes (FC) from ESE to MSE against log10 of p-values (paired t-test, n=6×2 samples). Proteins whose abundance change remained statistically significant after correcting for multiple testing are shown in black (<2-fold difference) and gray (≥2-fold difference).
Figure 4:
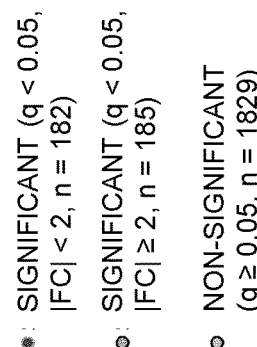

Using the paired design, 367 proteins were found with a significant (q≤0.05) abundance difference (fold change (FC) range: −15.2 to +60.9) in the UF of MSE versus ESE (FIG. 4), of which 185 proteins had at least two-fold abundance difference (|FC|≥2). Data mining of MSE up-regulated proteins (n=138) indicated that relative to the background human proteome, there was an enriched number of proteins participating in immune responses, blood coagulation and glycolysis (FIG. 2B) in MSE versus ESE UF (Gene Ontology term: 'Biological process'). Conversely, the number of proteins enriched for DNA replication, mRNA splicing and endoplasmic reticulum to Golgi vesicle-mediated transport was decreased in the UF transitioning from ESE to MSE (FIG. 2C).

Figure 5:
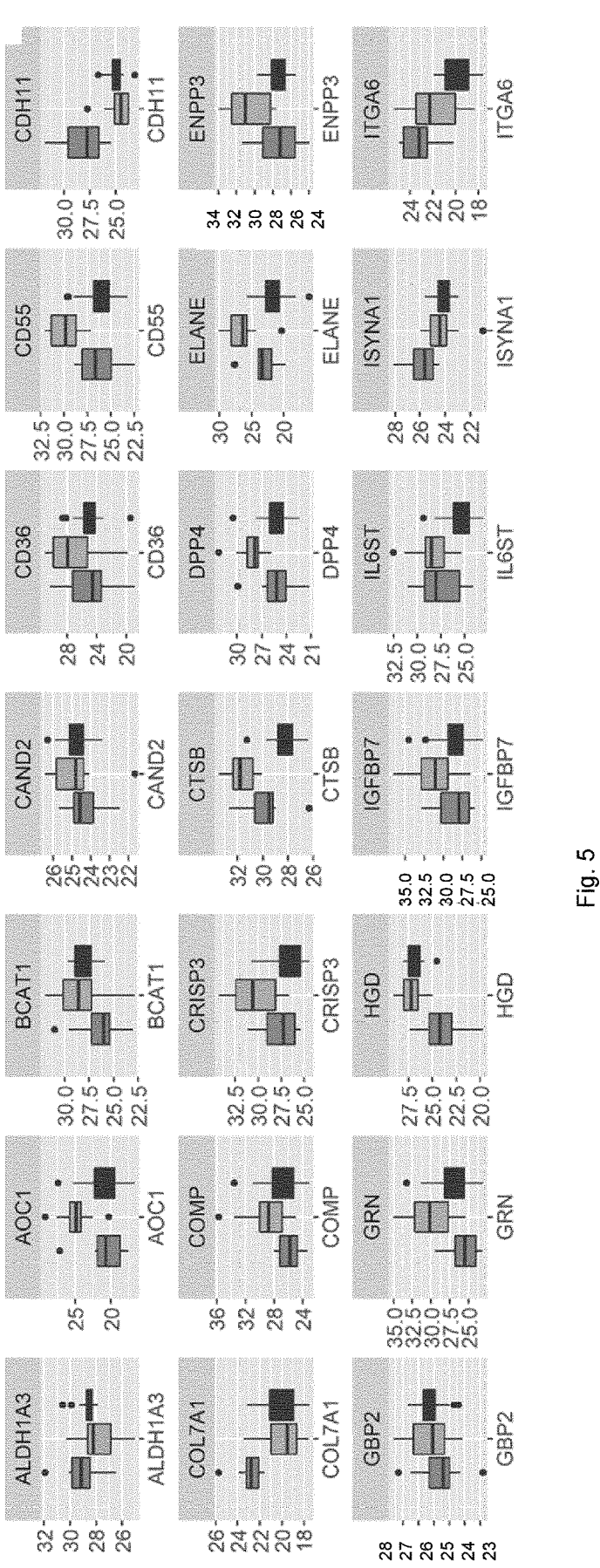
FIG. 5. Boxplots of log2 normalized intensity distributions of targeted proteins for control ESE (left bars) and MSE (middle bars) and RIF MSE (right bars) groups.
Figure 5:
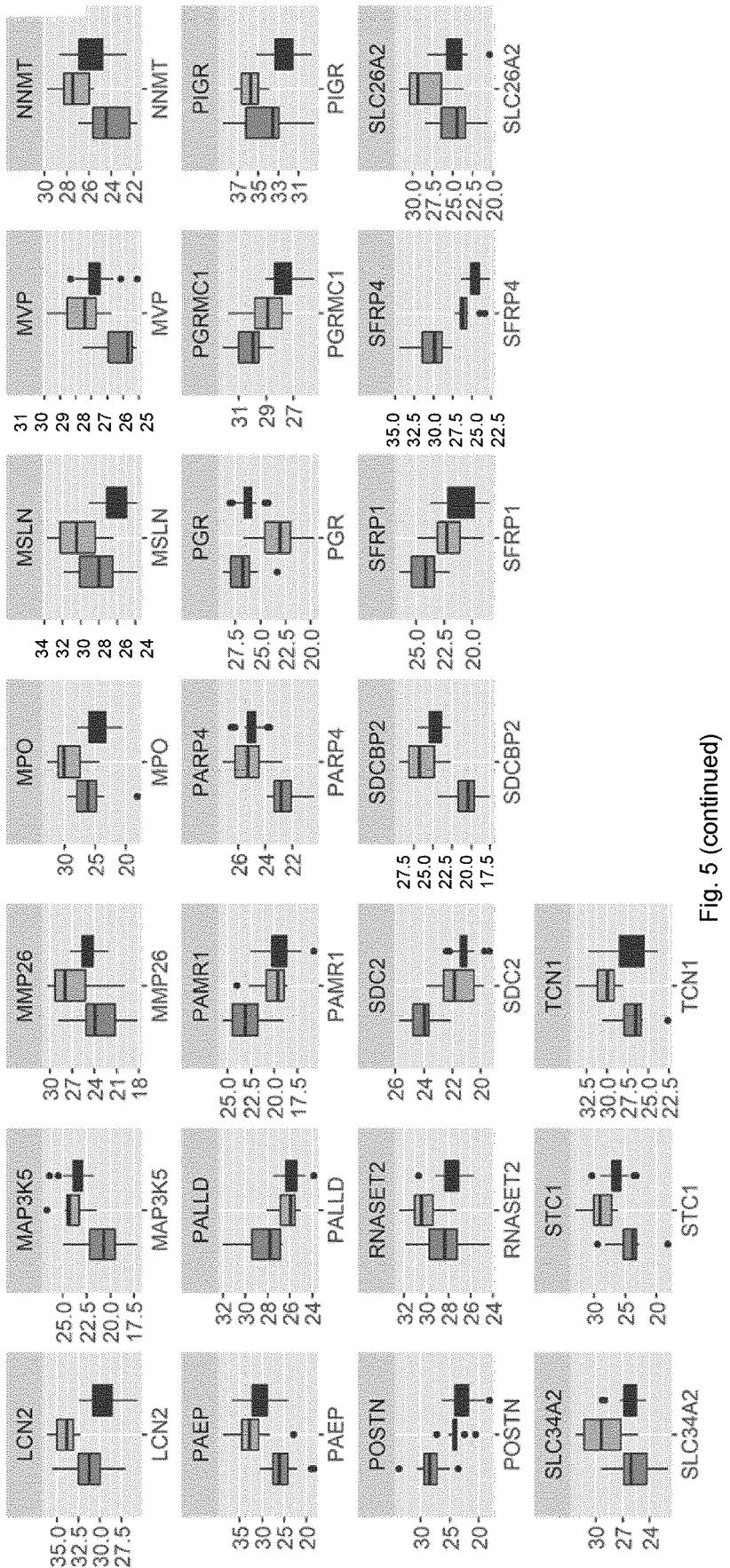
Figure 6A:
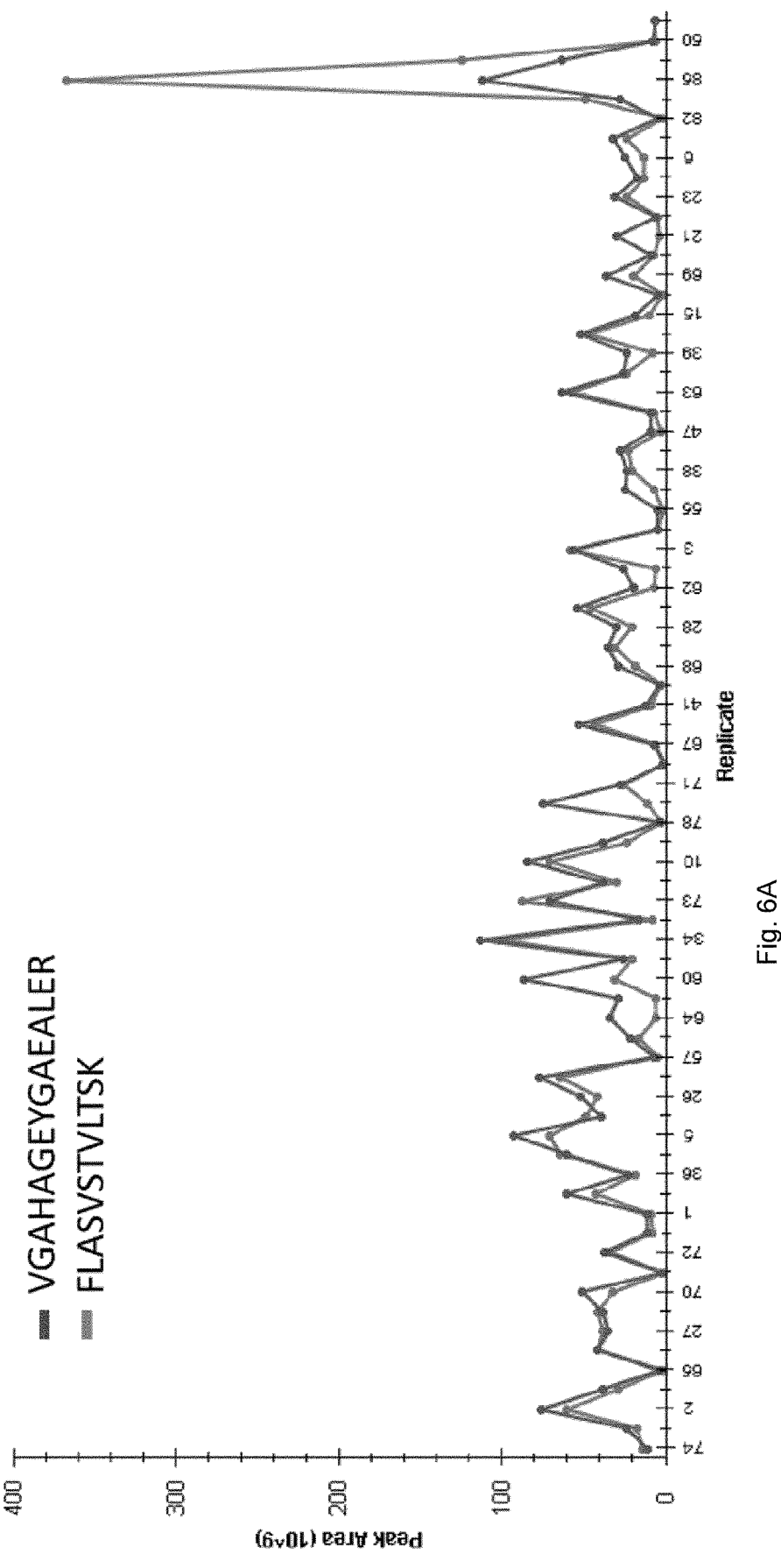
FIG. 6. (A) Peak areas of two peptides (SEQ ID NO: 27 and 28) from the hemoglobin subunit alpha (HBA1) show varying levels of blood contamination in uterine fluid samples. The peptides from HBA1 were measured via targeted mass spectrometry (MS). Non-normalized peak areas are presented. (B) Elongation factor 1-alpha 1 (EEF1A1) level in uterine fluid is not affected by blood contamination, as evidenced by insignificant correlation between EEF1A1 and HBA1.
Figure 6B:
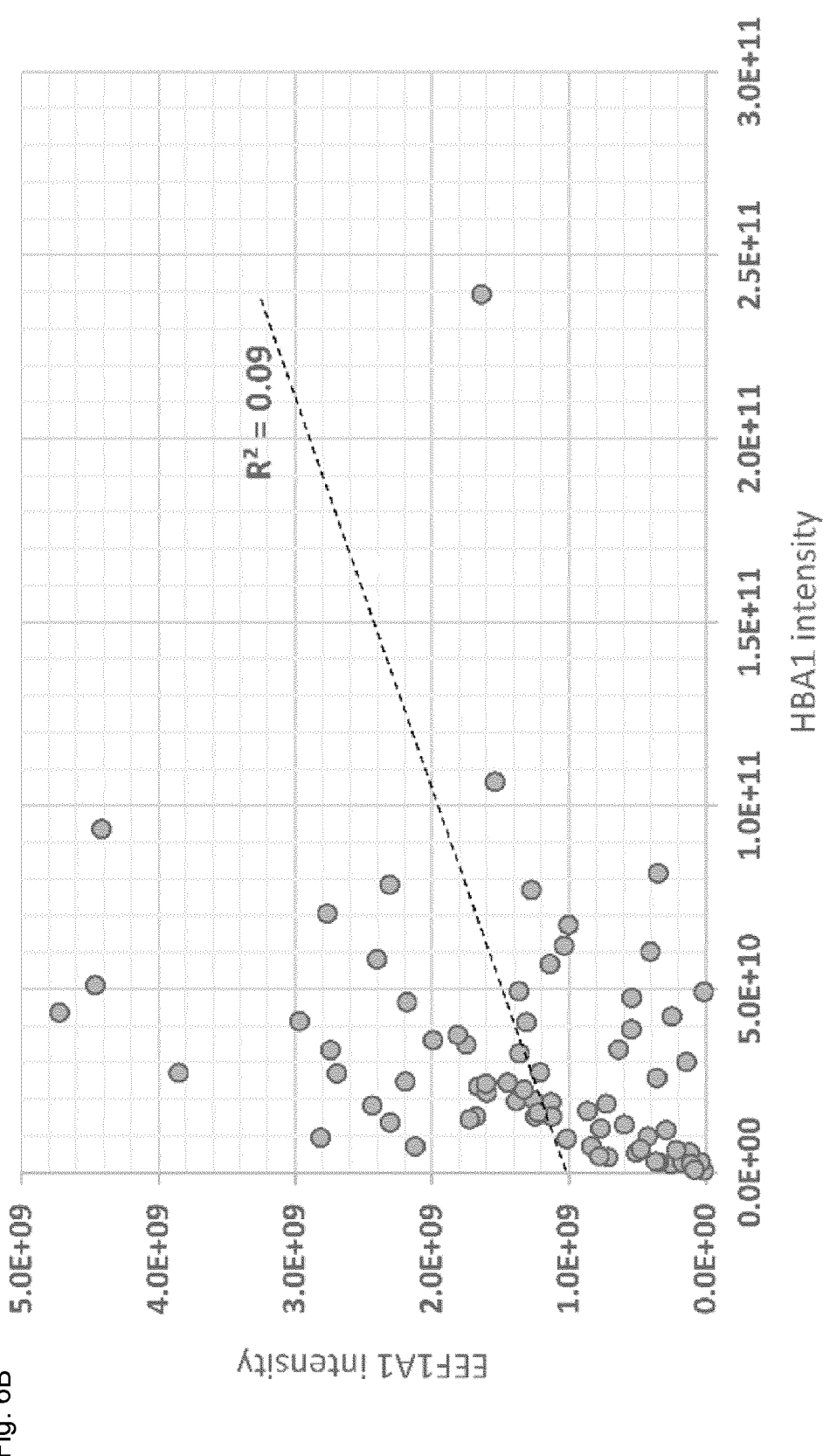

Targeted Validation of Candidate Protein Markers Underlines a Robust Set of Potential Receptivity-Associated Biomarkers Proteins having a large abundance difference (|FC|≥5, q<0.05, n=45) between ESE and MSE in our UF discovery dataset were selected (FIG. 5). Next, we determined which of the 45 proteins with a strong effect size would also be sufficiently robust for potential diagnostic use. A targeted MS assay was developed based on peptides identified in the discovery experiment (Table 6) and additional 11 volunteers were recruited from three different clinics for this experiment. It was observed that the clinical yield of fluid and its protein concentration tended to vary in obtained samples. Therefore, EEF1A1 protein was included for normalization into the targeted assay. EEF1A1 showed the most stable abundance across samples in the discovery experiment ($FC_{MSE/ESE}$=1.0, p=0.99, CV=0.7%). Nevertheless, EEF1A1 has been reported to be present in erythrocytes and, based on visual observations, UF samples tend to have varying degrees of contamination by hemolysed blood. Fluctuating level of HBA1 (hemoglobin alpha chain 1) were indeed observable in the validation samples (FIG. 6A), however, HBA1 explained only 9% of EEF1A1 variability in UF (FIG. 6B). Therefore, samples were not excluded based on HBA1 level alone, as varying blood contamination was somewhat inevitable during the sample collection process and its overall contribution to total EEF1A1 appeared marginal.

Figure 7A:
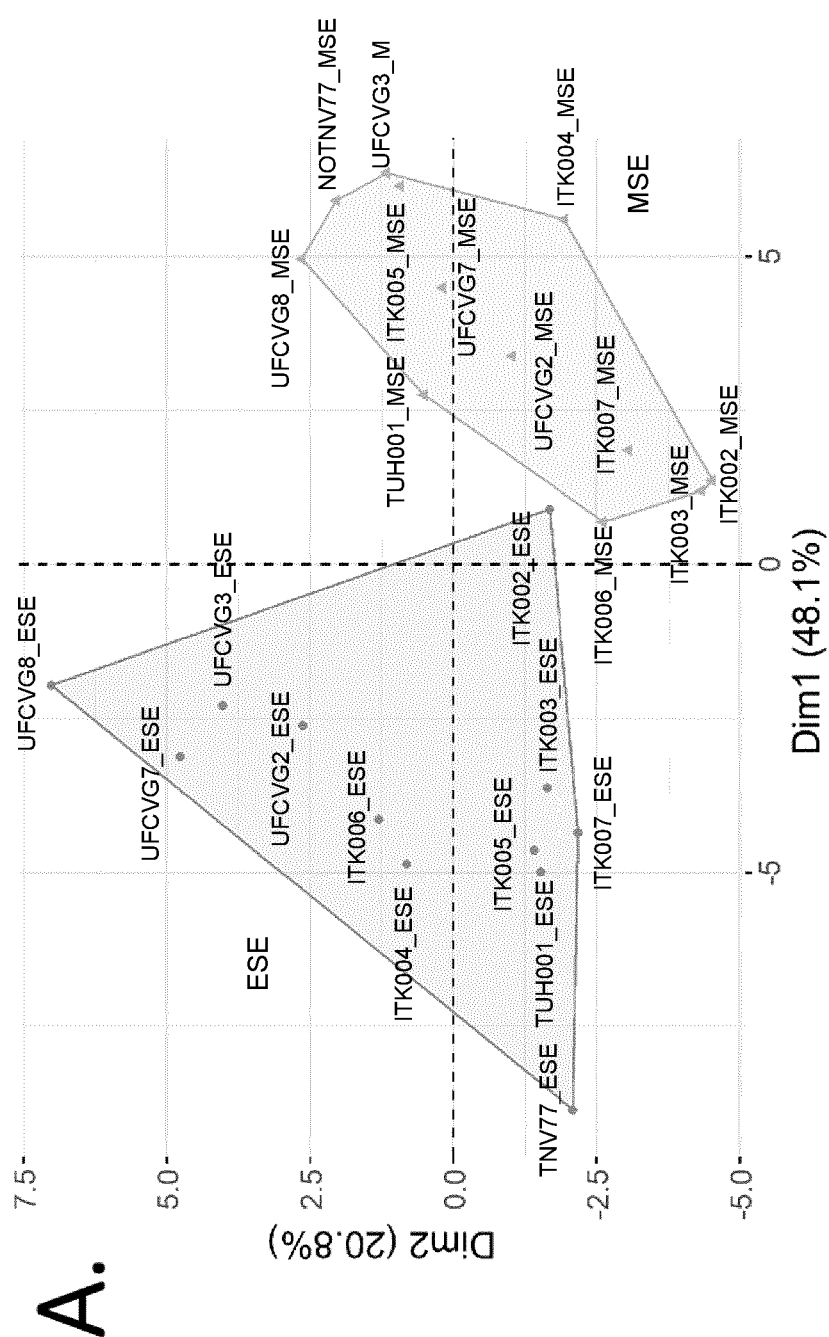
FIG. 7. (A) Validation proteins separate control ESE and MSE groups into distinct principal component analysis (PCA) spaces confirming their association with the respective cycle phases. (B) PCA analysis including RIF MSE samples. (C) Proteins highly significantly (p<0.005) different between control MSE and RIF MSE group RIF MSE more closely together with control ESE than control MSE samples. (D) Proteins indicative of WOI displacement in women with RIF. The y-axis in the boxplots denotes normalized and log2-transformed summed peptide intensities of the respective proteins (ESE: left bars, MSE: middle bars, RIF MSE: right bars).

Altogether, 38 out of 45 proteins that were selected for validation from the discovery experiment showed statistical significance (p<0.05) also in the validation cohort, and distinctly separated ESE and MSE groups in the PCA analysis (FIG. 7A, Table 5). The seven remaining proteins (CAND2, CD36, GBP2, IGFBP7, IL6ST, ITGA6, PIGR) did not display a significant difference between control ESE and MSE. This may be due to effects not persisting in a larger cohort and/or higher technical variability in the data, as sampled from multiple clinics were used for the validation instead of a single clinic used in the discovery set. Therefore, 38 out of the initial 45 proteins were considered validated and optimally robust indicators for further development.

Figure 7B:
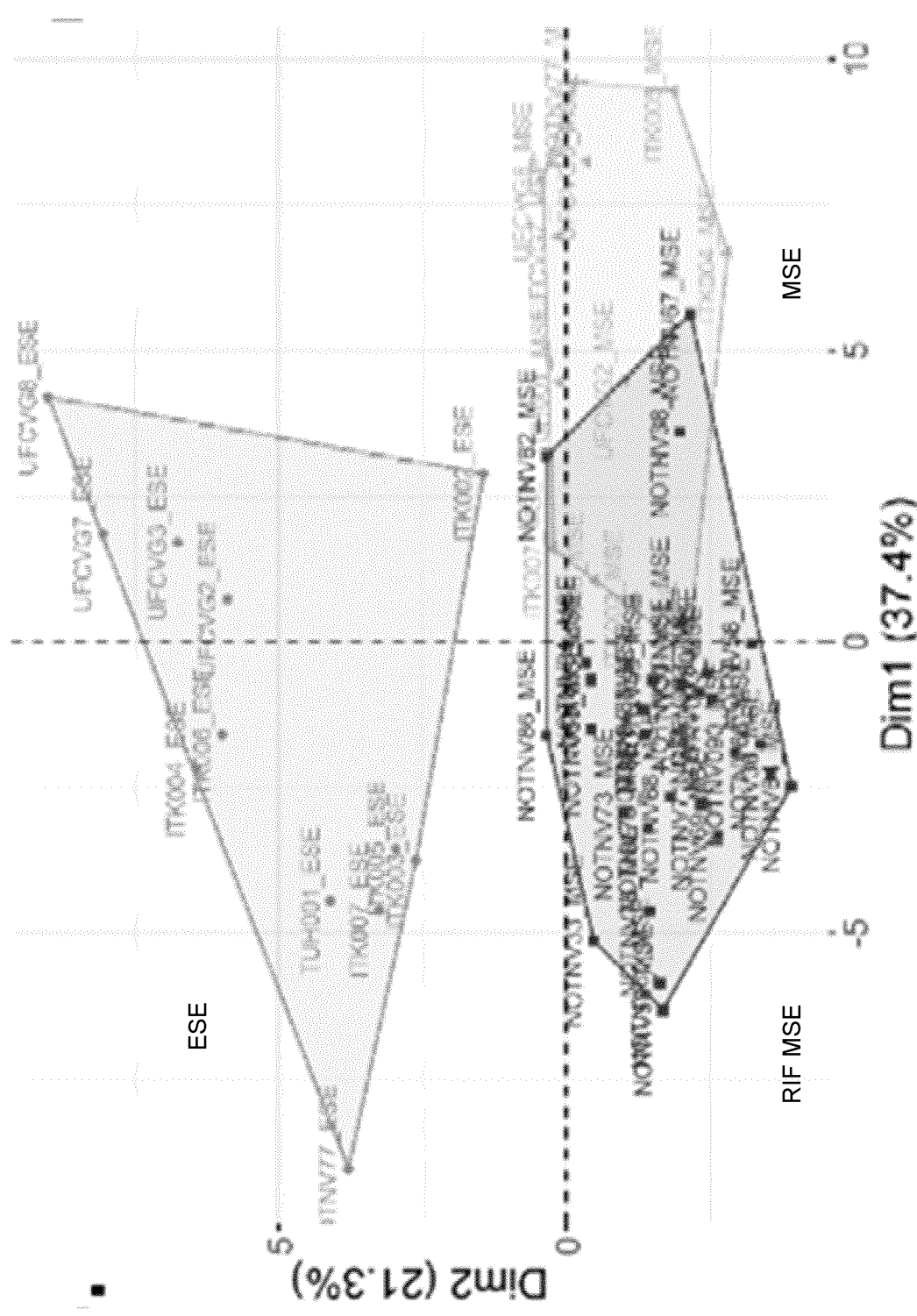
Figure 7C:
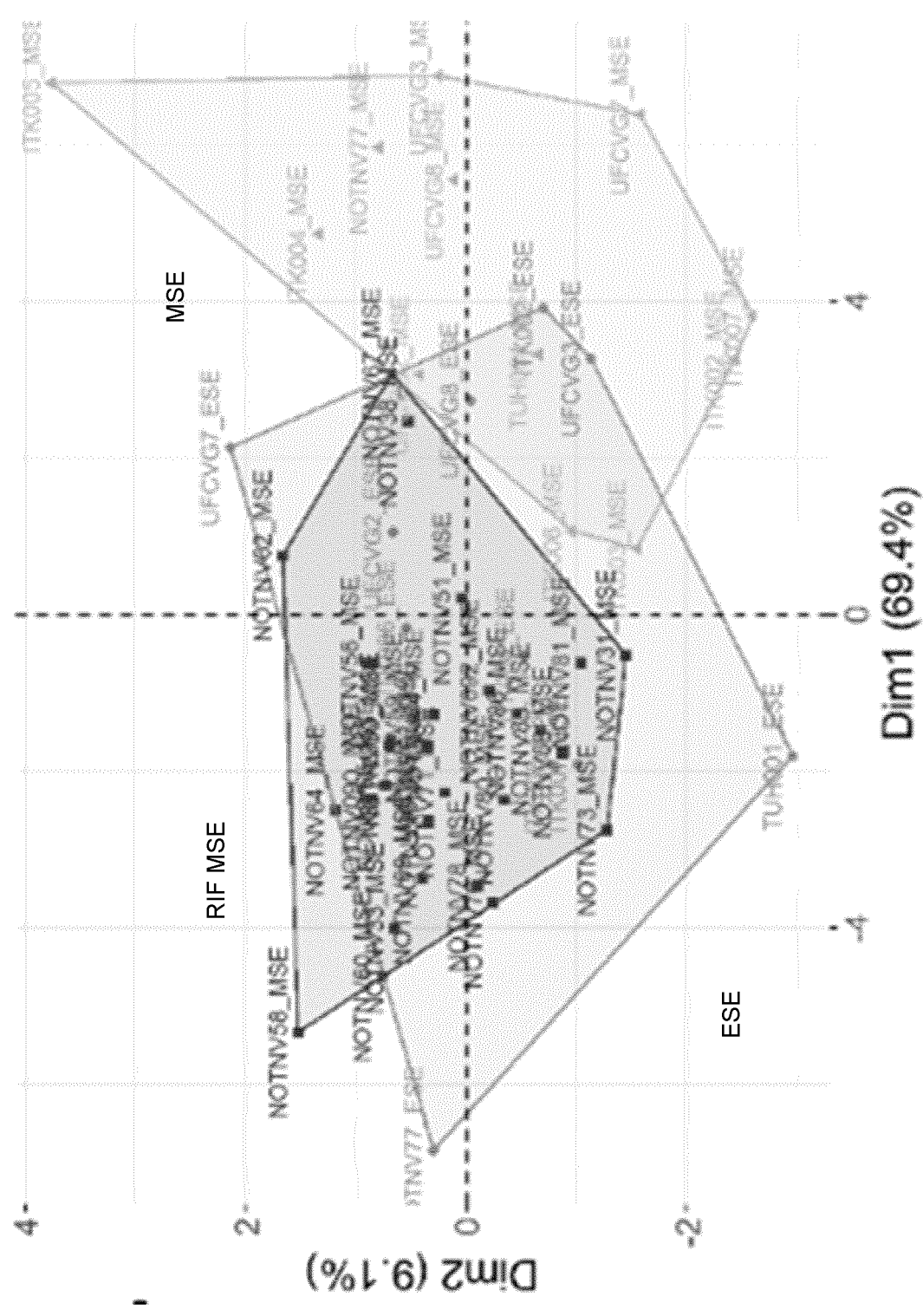
Figure 7D:
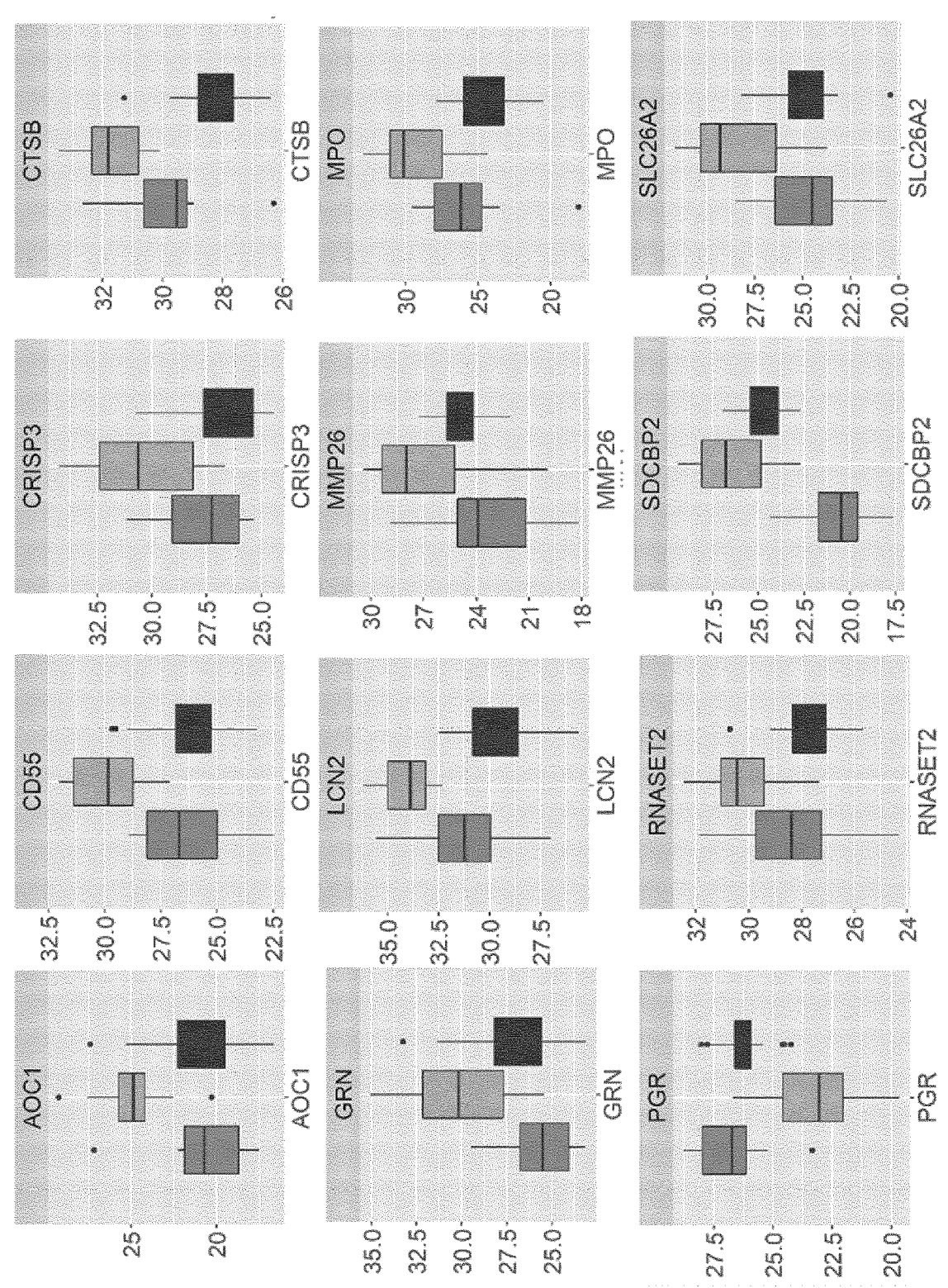
Figure 7D:
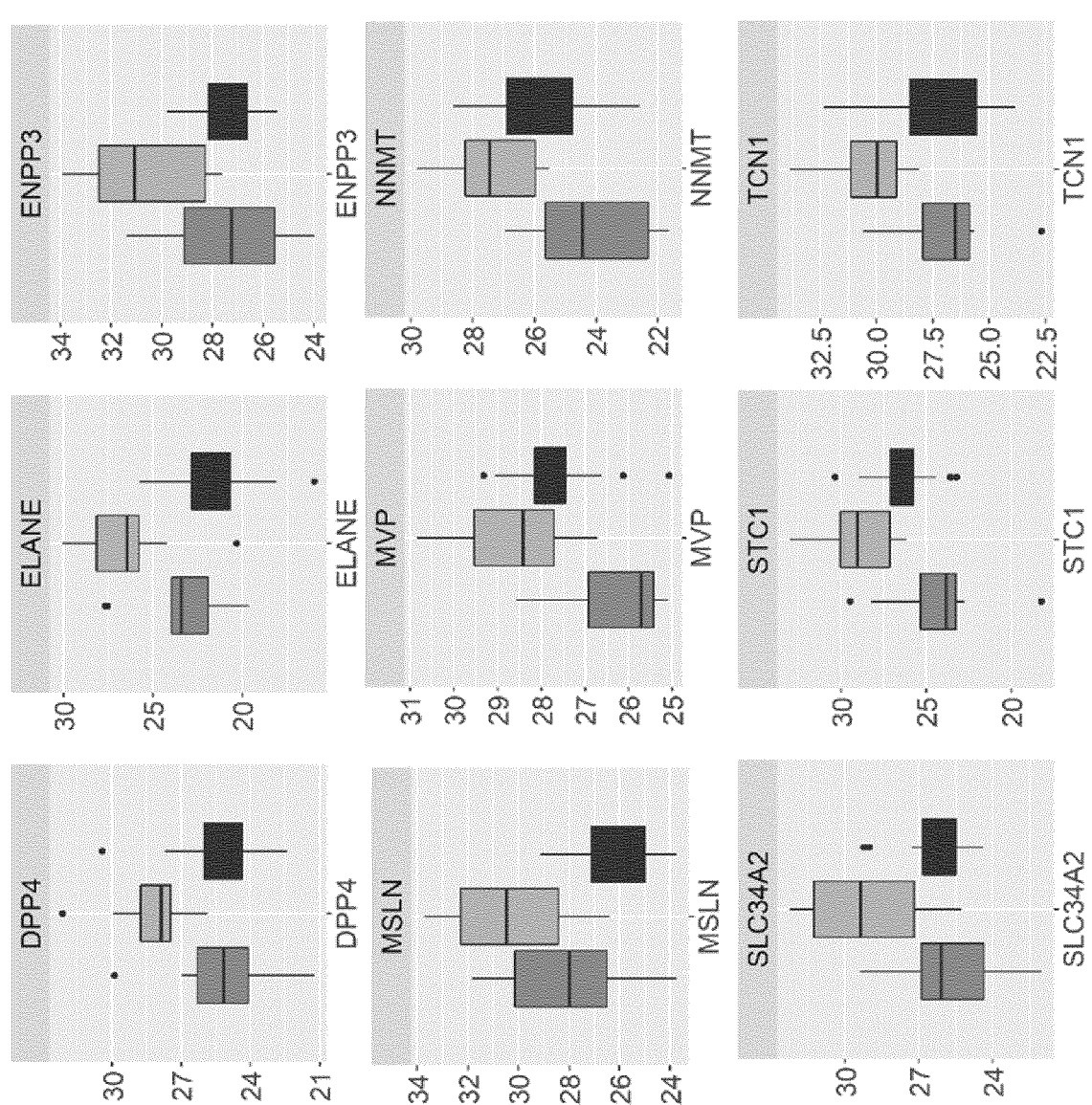

Evidence from Uterine Fluid Proteins for Displacement of the Window of Implantation in Women with Repeated Implantation Failure A cohort of women with RIF (n=29) was also included into the targeted measurements to see whether any of the discovery markers may be dysregulated in RIF patients during MSE when the EM is expected to be receptive for embryo implantation. PCA analysis indicated that there were three discernible groups with a partial overlap between control MSE and RIF MSE samples (FIG. 7B). However, it was evident from the data that more than half of the validated proteins (21/38) showed similar levels between control ESE and RIF MSE (FIGS. 7C and 7D). This observation was also illustrated in PCA analysis with proteins highly significantly (p<0.005) different between control MSE and RIF MSE where the RIF MSE group display more overlap with the control ESE than with the control MSE (FIG. 7C).

The signature from the ESE-like UF proteins in RIF MSE group pointed to the displacement of the WOI in women with RIF. Although, it should be noted that not all of the proteins included into the validation showed evidence for displaced expression in RIF and the levels of 17 of the 38 proteins (ALDH1A3, BCAT1, CDH11, COL7A1, COMP, HGD, ISYNA1, MAP3K5, PAEP, PALLD, PAMR1, PARP4, PGMRC1, POSTN, SDC2, SFRP1, SFRP4) were still similar between both MSE groups. Overall, a significant fraction (21/38) of the UF protein data points to a shifted WOI in women with RIF, where control ESE and RIF MSE share similar protein levels, Table 7.

TABLE 7

UF proteins indicative of WOI displacement in women with RIF

| Protein name | Gene name | UniProt accession | Fold change $FC_{MSE/ESE}$* (q-value) |
|---|---|---|---|
| Nicotinamide N-methyltransferase | NNMT | P40261 | +60.9 (0.011) |
| Transcobalamin-1 | TCN1 | P20061 | +46.4 (0.008) |
| Sulfate transporter | SLC26A2 | P50443 | +39.9 (0.03) |
| Ectonucleotide pyrophosphatase/ phosphodiesterase family member 3 | ENPP3 | O14638 | +39.1 (0.031) |
| Granulins | GRN | P28799 | +36.8 (0.025) |
| Stanniocalcin-1 | STC1 | P52823 | +33.9 (0.014) |
| Dipeptidyl peptidase 4 | DPP4 | P27487 | +32.4 (0.04) |
| Myeloperoxidase | MPO | P05164 | +31.8 (0.027) |
| Complement decay-accelerating factor | CD55 | P08174 | +29.6 (0.027) |
| Neutrophil elastase | ELANE | P08246 | +27.8 (0.046) |
| Sodium-dependent phosphate transport protein 2B | SLC34A2 | O95436 | +22.1 (0.048) |
| Neutrophil gelatinase-associated lipocalin | LCN2 | P80188 | +17.2 (0.018) |
| Mesothelin | MSLN | Q13421 | +16.3 (0.025) |
| Cathepsin B | CTSB | P07858 | +9.6 (0.03) |
| Ribonuclease T2 | RNASET2 | O00584 | +7.1 (0.034) |
| Cysteine-rich secretory protein 3 | CRISP3 | P54108 | +6.2 (0.034) |
| Major vault protein | MVP | Q14764 | +5.2 (0.011) |
| Matrix metalloproteinase-26 | MMP26 | Q9NRE1 | +5.0 (0.025) |
| Amiloride-sensitive amine oxidase [copper-containing] | AOC1 | P19801 | only MSE** |
| Syntenin-2 | SDCBP2 | Q9H190 | only MSE** |
| Progesterone receptor | PGR | P06401 | -8.5 (0.011) |

Figure 8:
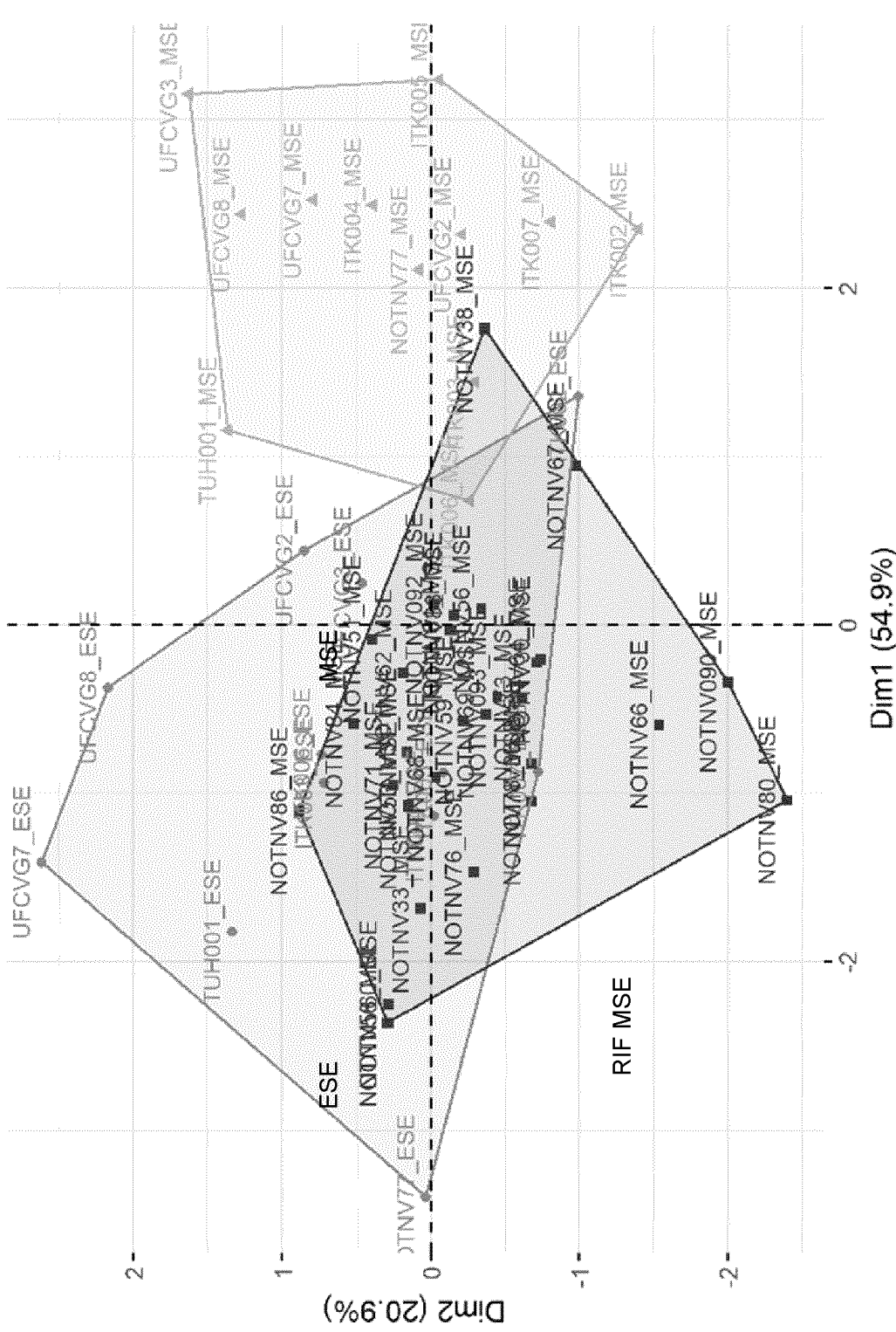
FIG. 8. Panel consisting of UF proteins LCN2, NNMT, PGR and SLC26A2 provides high specificity and sensitivity for separating the MSE samples from the ESE samples (ESE: left bars, MSE: middle bars, RIF MSE: right bars).
Figure 8:
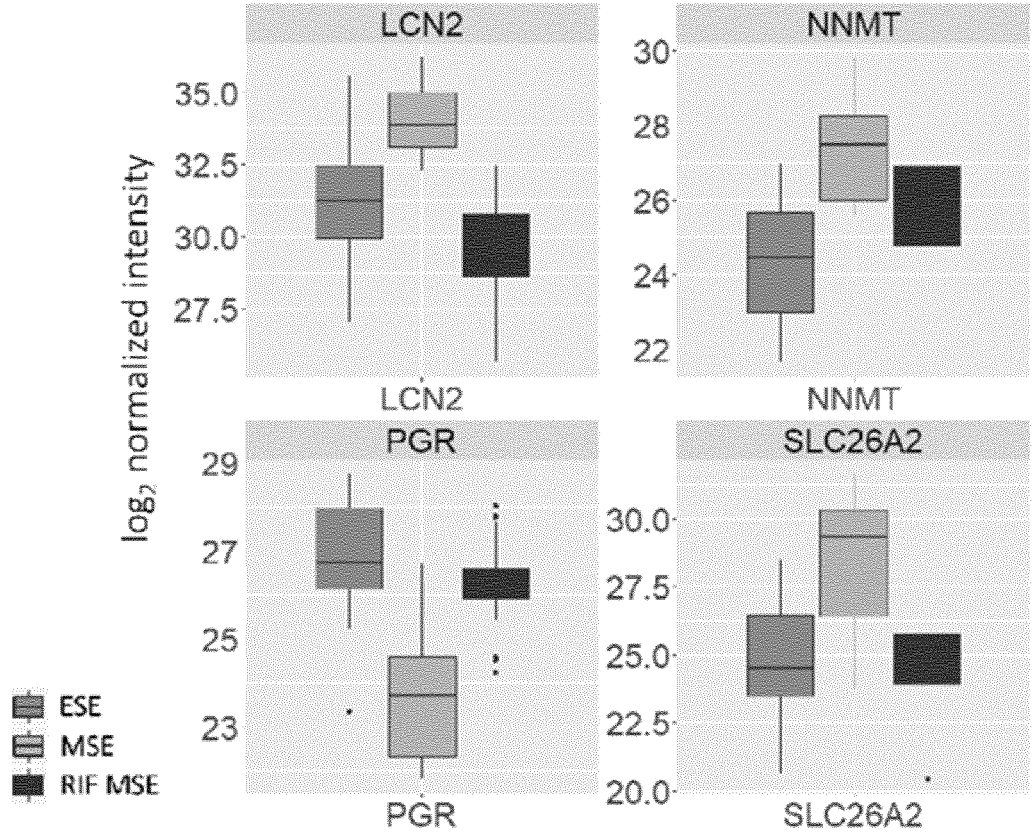

*Positive value indicates upregulation in MSE relative to ESE, negative value indicates down-regulation in MSE relative to ESE
**Protein only detected in either MSE or ESE
FC—fold change,
EM—endometrial A Four-Protein Diagnostic Panel Enables High Sensitivity and Specificity for Monitoring Receptivity from Uterine Fluid For determining an optimal set of proteins for differentiating receptive UF from a pre-receptive and RIF affected one, different three (1330 combinations) and four (5986 combinations) marker panels out of the 21 ESE-like proteins in RIF MSE described above were combinatorically analysed. For each possible combination specificity and sensitivity were calculated with Random Forest machine learning. A panel consisting of four proteins PGR, NNMT, SLC26A2 and LCN2 emerged as the most optimal by providing strong classification accuracy for distinguishing control MSE from control ESE (both specificity and sensitivity of 91.7%) while also enabling high separation of RIF MSE samples from control MSE (specificity and sensitivity of 91.7% and 96.6%, respectively) (FIG. 8). The levels of all these four proteins were more similar to control ESE than to control MSE, thus indicating a pre-receptive EM in the RIF cohort.

Discussion

Estimating EM receptivity for optimal embryo transfer is of high importance to improve the success rates of IVF and to better understand the causes behind RIF. Accumulating evidence points that for RIF, shifted WOI may be a common (~16-26% of cases) etiologic factor. The use of tissue transcriptomic assays to determine the exact day of WOI has improved diagnosis of RIF-cases for whom a personalized embryo transfer (pET) results in improved implantation and pregnancy rate. Gene expression profiling is also more accurate than histological dating. However, the invasive nature of the current EM tissue-based assays makes them unsuitable for pET in the same cycle. A proof-of-principle study estimating UF cellular mRNA patterns for EM receptivity has also been described. However, this was achieved only with RNA amplification and subsequent microarray analysis (Chan et al. 2013). These aspects render the process cumbersome and potentially less reproducible from lab-to-lab. Microarrays, and now more commonly mRNA sequencing, are also costly and require more expertise compared to protein-directed immunoassays, e.g., ELISA, which can be performed in an automated manner in most clinics within the same day.

The UF proteome is a complex and dynamic mixture of different proteins, as evidence was found for over 3,000 proteins of which roughly a tenth (367) underwent significant alterations while transitioning from ESE to MSE. Most of the UF total proteome was made up of extracellular, secreted or plasma membrane proteins (FIG. 2A). However, there appeared to be a number of proteins in the fluid that by current understanding are intracellular. It is possible that they are also the constituents of extracellular vesicles, which are well known to be present in UF. Relative to glandular cell proteome, exosomal proteins were enriched in the UF data (FIG. 2A) and known exosomal markers CD9, CD81 and CD63 were detected in UF, thereby supporting the likely presence of exosomes in the samples. By magnitude of expressional abundance, we stratified and focused further on 45 proteins that showed large ($|FC| \geq 5$) and significant changes transitioning from ESE to MSE (FIG. 5). These proteins were also verified to be significantly different between ESE and MSE by targeted MS in the independent validation cohort (Table 5).

Targeted MS analysis of the 45 proteins under focus revealed that not all of them may be directly suitable for clinical development, as 38 of them showed significance for changed level between ESE and MSE in validation. In clinical setting, reproducibility of fluid collection can be lower due to difficult to control factors, e.g., procedural differences employed by the physicians, biological variability etc. Therefore, the final validated panel should reflect only markers that are not easily susceptible to confounders, and, are sufficiently robust for estimating receptivity from UF. All of the 38 validated proteins showed change in the same direction as the discovery measurements and distinguished ESE and MSE samples into separate groups (FIG. 7A) with proteins, such as SFRP4, PALLD, MVP SDCBP2, PGR, NNMT and PARP4 differing most significantly ($p<0.001$).

It was hypothesized that women with RIF, for whom uterine factor infertility is highly suspected, could show alterations in UF protein levels selected for the targeted analysis. In fact, we found that for a large (21/45) subset of proteins the levels are instead similar to control ESE levels suggesting a shifted WOI (FIGS. 7C and 7D).

As one of the main aims of the study was to propose a protein set from UF for estimating EM receptivity as a non-invasive alternative to tissue mRNA, we sought to determine which marker combinations would provide highest specificity and sensitivity and would also be feasible for future development into a simple ELISA-type of an assay, i.e., marker panel with preferably no more than four proteins. PCA and Random Forest machine learning were combined to suggest the best markers for EM receptivity monitoring. A panel consisting of proteins PGR, NNMT, SLC26A2 and LCN2 gave the optimal balance of accuracies between classifications of ESE versus MSE (specificity and sensitivity of 91.7%) and MSE versus RIF MSE (specificity of 91.7% and sensitivity of 96.6%) (FIG. 8). A strikingly elevated level of progesterone receptor (PGR) was evident in the UF of the RIF cohort during the MSE phase of the menstrual cycle where its levels were significantly down-regulated in control women. PGR is one of the main nodes between the signals from the endocrine system to the EM.

NNMT (nicotinamide N-methyltransferase) is well-known for the metabolism of nicotinamide and various xenobiotics. Its expression in EM cells appears to be steroid hormone (estradiol and progesterone) dependent, is impaired as a result of progesterone resistance and is down-regulated during the WOI in women with RIF. NNMT increases cellular migration/invasiveness, tumor development and is also constitutively over-expressed in ectopic endometriotic stromal cells. SLC26A2, or the sulphate ion transporter, is also inducible by progesterone. SLC26A2 is impaired during WOI in women with PCOS. LCN2, a neutrophil gelatinase-associated lipocalin, was highly significantly lower in the RIF MSE cohort compared to control, supporting its relevance to successful implantation.

In conclusion, this proteomic investigation into uterine fluid's potential for a less-invasive EM receptivity monitoring demonstrated that sufficient robustness, sensitivity and specificity can be achieved by measuring only a small subset of proteins present in the fluid. The findings provide novel and supporting data to the study of RIF pathogenesis.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Benjamini and Hochberg, Controlling the False Discovery Rate—a Practical and Powerful Approach to Multiple Testing, *J R Stat Soc B* 1995; 57(1): 289-300

Breiman, Random forests, *Machine Learning* 2001; 45(1): 5-32

Chan et al., Discovery of biomarkers of endometrial receptivity through a minimally invasive approach: a validation study with implications for assisted reproduction, *Fertility and sterility* 2013; 100(3): 810-817

Cox and Mann, MaxQuant enables high peptide identification rates, individualized p.p.b.-range mass accuracies and proteome-wide protein quantification, *Nature biotechnology* 2008; 26(12): 1367-1372

Escher et al., iRT, a normalized retention time for more targeted measurement of peptides, *Proteomics* 2012; 12(8): 1111-1121

Galgani et al., Regulatory T cells, inflammation, and endoplasmic reticulum stress in women with defective endometrial receptivity, *Fertility and sterility* 2015; 103(6): 1579-1586 e1571

Kasvandik et al., Deep Quantitative Proteomics Reveals Extensive Metabolic Reprogramming and Cancer-Like Changes of Ectopic Endometriotic Stromal Cells, *Journal of proteome research* 2016; 15(2): 572-584

Le et al., An R package for multivariate analysis, *J Stat Softw* 2008; 25(1): 1-18

MacLean et al., Skyline: an open source document editor for creating and analyzing targeted proteomics experiments, *Bioinformatics* 2010; 26(7): 966-968

Oberg and Vitek, Statistical design of quantitative mass spectrometry-based proteomic experiments, *Journal of proteome research* 2009; 8(5): 2144-2156

Pathan et al., FunRich: An open access standalone functional enrichment and interaction network analysis tool, *Proteomics* 2015; 15(15): 2597-2601

Storey and Tibshirani, Statistical significance for genome-wide studies, *Proceedings of the National Academy of Sciences of the United States of America* 2003; 100 (16): 9440-9445

The invention claimed is:

1. A method for treatment comprising implanting an embryo in a human female subject that has been identified as having a receptive endometrium, the method comprising:

measuring, in a uterine fluid (UF) sample taken from the human female subject, a respective amount of at least three proteins selected from the group consisting of nicotinamide N-methyltransferase encoded by the gene NNMT, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2;

comparing the respective amount with a respective control amount of the at least three proteins;

determining the human female subject has a receptive endometrium by determining that the human female subject is in a mid-secretory (MSE) phase wherein, for each protein of the at least three proteins, the respective amount of the protein is lower than the control amount if the protein is progesterone receptor encoded by the gene PGR and the respective amount of the protein is higher than the control amount if the protein is selected from the group consisting of nicotinamide N-methyltransferase encoded by the gene NNMT, neutrophil gelatinase-associated lipocalin encoded by the gene LCN2, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2; and implanting an embryo in the human female subject determined to have a receptive endometrium.

2. The method according to claim 1, wherein measuring the respective amount comprises measuring, in the UF sample taken from the human female subject, the respective amount of nicotinamide N-methyltransferase encoded by the gene NNMT and the respective amount of at least two proteins selected from the group consisting of, neutrophil gelatinase-associated lipocalin encoded by the gene LCN2, progesterone receptor encoded by the gene PGR, sulfate transporter encoded by the gene SLC26A2, sodium-dependent phosphate transport protein 2B encoded by the gene SLC34A2, transcobalamin-1 encoded by the gene TCN1, ectonucleotide pyrophosphatase/phosphodiesterase family member 3 encoded by the gene ENPP3, granulins encoded by the gene GRN, stanniocalcin-1 encoded by the gene STC1, dipeptidyl peptidase 4 encoded by the gene DPP4, myeloperoxidase encoded by the gene MPO, complement decay-accelerating factor encoded by the gene CD55, neutrophil elastase encoded by the gene ELANE, mesothelin encoded by the gene MSLN, cathepsin B encoded by the gene CTSB, ribonuclease T2 encoded by the gene RNASET2, cysteine-rich secretory protein 3 encoded by the gene CRISP3, major vault protein encoded by the gene MVP, matrix metalloproteinase-26 encoded by the gene MMP26, amiloride-sensitive amine oxidase copper-containing encoded by the gene AOC1, and syntenin-2 encoded by the gene SDCBP2.

3. The method according to claim 2, wherein measuring the respective amount comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR; and comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR.

4. The method according to claim 3, wherein measuring the respective amount comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR and an amount of sulfate transporter encoded by the gene SLC26A2 and/or of sodium-dependent phosphate transport protein 2B encoded by the gene SLC34A2; and comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR and control amount of sulfate transporter encoded by the gene SLC26A2 and/or of sodium-dependent phosphate transport protein 2B encoded by the gene SLC34A2.

5. The method according to claim 4, wherein measuring the respective amount comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR and the amount of sulfate transporter encoded by the gene SLC26A2; and comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR and control amount of sulfate transporter encoded by the gene SLC26A2.

6. The method according to claim 2, wherein measuring the respective amount comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR and an amount of sulfate transporter encoded by the gene SLC26A2 and/or of sodium-dependent phosphate transport protein 2B encoded by the gene SLC34A2; and comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR and control amount of sulfate transporter encoded by the gene SLC26A2 and/or of sodium-dependent phosphate transport protein 2B encoded by the gene SLC34A2.

7. The method according to claim 6, wherein measuring the respective amount comprises measuring, in the UF sample taken from the human female subject, the respective amount of nicotinamide N-methyltransferase encoded by the gene NNMT, neutrophil gelatinase-associated lipocalin encoded by the gene LCN2, progesterone receptor encoded by the gene PGR and the amount of sulfate transporter encoded by the gene SLC26A2; and comparing the respective amount comprises comparing the respective amount with the respective control amount of nicotinamide N-methyltransferase encoded by the gene NNMT, neutrophil gelatinase-associated lipocalin encoded by the gene LCN2, progesterone receptor encoded by the gene PGR and control amount of sulfate transporter encoded by the gene SLC26A2.

8. The method according to claim 1, wherein measuring the respective amount comprises measuring, in the UF sample taken from the human female subject, the respective amount of at least three but no more than six proteins selected from the group; and comparing the respective amount comprises comparing the respective amount with the respective control amount of the at least three but no more than six proteins.

9. The method according to claim 1, wherein measuring the respective amount comprises measuring, in the UF sample taken from the human female subject, the respective amount of the at least three proteins selected from the group using a respective antibody that specifically binds to the respective protein of the at least three proteins selected from the group.

10. The method according to according to claim 1, wherein measuring the respective amount comprises:

separating proteins from the UF sample taken from the human female subject on a two-dimensional gel electrophoresis gel;

identifying the at least three proteins selected from the group on the two-dimensional gel electrophoresis gel; and measuring a respective amount of the identified at least three proteins selected from the group on the two-dimensional gel electrophoresis gel.

11. The method according to claim 1, further comprising:

measuring, in the UF sample taken from the human female subject, an amount of elongation factor 1-alpha 1 (EEF1A1); and normalizing the respective amount of the at least three proteins based on the amount of EEF1A1, wherein comparing the respective amount comprises comparing the respective normalized amount with a respective control amount of the at least three proteins.

* * * * *